(12) United States Patent
Kabanov et al.

(10) Patent No.: US 6,353,055 B1
(45) Date of Patent: *Mar. 5, 2002

(54) POLYNUCLEOTIDE COMPOSITIONS

(75) Inventors: Alexander Victorovich Kabanov, Omaha, NE (US); Valery Yulievich Alakov, D'Urfe (CA); Sergey V. Vingogradov, Omaha, NE (US)

(73) Assignee: Supratek Pharma Inc., Quebec (CA)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/912,968

(22) Filed: Aug. 1, 1997

Related U.S. Application Data

(63) Continuation-in-part of application No. 08/342,209, filed on Nov. 18, 1994, now Pat. No. 5,656,611.

(51) Int. Cl.$^7$ .......................... C08L 53/00; C07H 21/04; A61K 31/70

(52) U.S. Cl. .................. 525/92 A; 525/92 L; 525/540; 525/54.2; 514/44; 536/23.7; 536/23.72; 536/24.5

(58) Field of Search ....................... 524/612; 525/92 A, 525/92 L, 540, 54.2; 514/44; 536/23.7, 23.72, 24.5

(56) References Cited

U.S. PATENT DOCUMENTS

| | | | |
|---|---|---|---|
| 4,027,013 A | * | 5/1977 | Bick et al. |
| 4,188,373 A | * | 2/1980 | Krezanoski |
| 4,347,339 A | * | 8/1982 | Boevink et al. ............ 525/540 |
| 4,474,752 A | | 10/1984 | Haslam et al. |
| 4,609,546 A | * | 9/1986 | Hiratani |
| 4,673,729 A | * | 6/1987 | Schroer et al. ............. 524/612 |
| 4,740,498 A | * | 4/1988 | Hirao et al. |
| 4,772,466 A | * | 9/1988 | Alison et al. |
| 4,801,452 A | | 1/1989 | Hunter et al. ............ 424/94.63 |
| 4,837,014 A | | 6/1989 | Hunter et al. |
| 4,865,835 A | * | 9/1989 | Begent |
| 4,873,083 A | | 10/1989 | Hunter et al. ................. 424/83 |
| 4,879,109 A | | 11/1989 | Hunter ........................ 424/83 |
| 4,882,168 A | | 11/1989 | Casey et al. |
| 4,897,263 A | | 1/1990 | Hunter |
| 4,937,070 A | | 6/1990 | Hunter |
| 4,957,735 A | * | 9/1990 | Huang |
| 4,997,644 A | | 3/1991 | Hunter |

(List continued on next page.)

FOREIGN PATENT DOCUMENTS

| | | |
|---|---|---|
| EP | 0211601 | 2/1997 |
| WO | WO 86/07539 | 12/1986 |
| WO | WO 88/01873 | 3/1988 |
| WO | WO 88/06038 | 8/1988 |
| WO | WO89/00812 | 2/1989 |
| WO | WO 91/16058 | 10/1991 |
| WO | WO 92/00101 | 1/1992 |
| WO | WO 92/16484 | 10/1992 |
| WO | WO 94/08564 | 10/1993 |
| WO | WO94/08564 | 4/1994 |
| WO | WO95/03829 | 2/1995 |
| WO | WO96/15778 | 5/1996 |
| WO | WO 96/40056 | 6/1996 |
| WO | WO96/00801 | 7/1996 |
| WO | WO 96/16541 | 7/1996 |
| WO | WO 96/40055 | 12/1996 |
| WO | WO96/40056 | 12/1996 |
| WO | WO99/39731 | 8/1999 |

OTHER PUBLICATIONS

Mortensen and Pedersen, *Macromolecules* (1993), 26:805–812.
Linse, *Macromolecules* (1993), 26:4437–4449.
Mortensen and Brown, *Macromolecules* (1993), 26:4128–4135.
Schillen et al., *Macromolecules* (1994), 27:4825–4832.
Schillen et al., *Macromolecules* (1993), 26:3611–3614.
Linse, *Macromolecules* (1994), 27:2685–2693.
Zhou and Chu, *Macromolecules* (1994), 27:2025–2033.
Zhou and Chu, *Journal of Colloid and Interface Science* (1988), 126:171–180.
Zhou and Chu, *Macromolecules* (1988), 21:2548–2554.
Alexandridis, *Macromolecules* (1994), 27:2414–2425.
Alexandridis, *Langmuir* (1994), 10:2604–2612.
Hecht and Hoffman, *Langmuir* (1994), 10:86–91.
Schmolka, *Journal of the Am. Oil Chemists' Society* (1977), 54:110–116.
Wilhelm et al., *Macromolecules* (1991), 24:1033–1040.
Hoes et al., *J. Controlled Release* (1995), 2:205–213.
Duncan et al., *J. Controlled Release* (1989), 10:51–63.
Pratesi et al., *Br. J. Cancer* (1985), 52:841–848.
Page and Alakhov, *Proc Ann Meet Am. Assoc Cancer Res* (1992), 33:A3302.
Summary of article in *Nikkei Weekly*, Feb. 1994.
Slepnev et al., *Biochemistry International*, (1992) 26:587–595.
Kabanov et al., *Biochemistry International*, (May, 1992) 26:1035–1042.

(List continued on next page.)

Primary Examiner—Peter Szekely
(74) Attorney, Agent, or Firm—Mathews, Collins, Shepherd & Gould, P.A.

(57) ABSTRACT

The invention provides compositions for stabilizing polynucleic acids and increasing the ability of polynucleic acids to cross cell membranes and act in the interior of a cell. In one aspect, the invention provides a polynucleotide complex between a polynucleotide and certain polyether block copolymers. Preferably, the polynucleotide complex will further include a polycationic polymer. The compositions can further include suitable targeting molecules and surfactants. In another aspect, the invention provides a polynucleotide complex between a polynucleotide and a block copolymer comprising a polyether block and a polycation block. In yet another aspect, the invention provides polynucleotides 10 that have been covalently modified at their 5' or 3' end to attach a polyether polymer segment.

11 Claims, No Drawings

U.S. PATENT DOCUMENTS

| | | | | |
|---|---|---|---|---|
| 5,017,370 | A | 5/1991 | Hunter et al. | 424/83 |
| 5,028,599 | A | 7/1991 | Hunter | |
| 5,030,448 | A | 7/1991 | Hunter | 424/83 |
| 5,032,394 | A | 7/1991 | Hunter | |
| 5,039,520 | A | 8/1991 | Hunter | |
| 5,041,288 | A | 8/1991 | Hunter | 424/83 |
| 5,047,236 | A | 9/1991 | Hunter et al. | 424/83 |
| 5,064,643 | A | 11/1991 | Hunter et al. | |
| 5,071,649 | A | 12/1991 | Hunter | |
| 5,078,995 | A | 1/1992 | Hunter et al. | |
| 5,080,894 | A | 1/1992 | Hunter et al. | |
| 5,089,260 | A | 2/1992 | Hunter et al. | |
| 5,114,708 | A | 5/1992 | Hunter et al. | |
| 5,152,979 | A | 10/1992 | Hunter | |
| 5,182,106 | A | 1/1993 | Mezrow et al. | |
| 5,183,687 | A | 2/1993 | Hunter et al. | |
| 5,198,211 | A | 3/1993 | Hunter et al. | |
| 5,234,683 | A | 8/1993 | Hunter et al. | |
| 5,240,701 | A | 8/1993 | Hunter et al. | |
| 5,240,702 | A | 8/1993 | Hunter et al. | |
| 5,250,294 | A | 10/1993 | Hunter et al. | |
| 5,412,072 | A | 5/1995 | Sakurai et al. | |
| 5,417,982 | A * | 5/1995 | Modi | |
| 5,436,170 | A * | 7/1995 | Cornell et al. | |
| 5,449,513 | A * | 9/1995 | Yokoyama et al. | |
| 5,462,990 | A * | 10/1995 | Hubbell et al. | 525/54.2 |
| 5,466,445 | A | 11/1995 | Hunter | |
| 5,470,568 | A | 11/1995 | Lee | |
| 5,488,034 | A | 1/1996 | McGregor et al. | |
| 5,494,660 | A | 2/1996 | Hunter et al. | |
| 5,523,492 | A | 6/1996 | Emanuele et al. | |
| 5,531,925 | A | 7/1996 | Landh et al. | |
| 5,554,372 | A | 9/1996 | Hunter | |
| 5,567,859 | A | 10/1996 | Emanuele et al. | |
| 5,573,934 | A | 11/1996 | Hubbell et al. | |
| 5,591,715 | A | 1/1997 | Coon et al. | |
| 5,593,658 | A * | 1/1997 | Bogdanov et al. | |
| 5,622,649 | A | 4/1997 | Hunter et al. | |
| 5,648,071 | A | 7/1997 | Hunter et al. | |
| 5,656,611 | A * | 8/1997 | Kabanov et al. | 514/44 |
| 5,674,911 | A | 10/1997 | Emanuele et al. | |
| 5,691,387 | A | 11/1997 | Emanuele et al. | |
| 5,696,090 | A | 12/1997 | McGregor et al. | |
| 5,696,298 | A | 12/1997 | Emanuele et al. | |
| 5,698,529 | A * | 12/1997 | Alakhov et al. | |
| 5,776,891 | A | 7/1998 | Coon et al. | |
| 5,783,178 | A | 7/1998 | Kabanov et al. | |
| 5,817,321 | A | 10/1998 | Alakhov et al. | |
| 5,840,319 | A * | 11/1998 | Alakhov et al. | |
| 5,885,590 | A * | 3/1999 | Hunter et al. | |
| 6,040,295 | A | 3/2000 | Rolland et al. | |

OTHER PUBLICATIONS

Kabanov et al., *FEBS Letters*, (Dec. 1989) 258:343–345.

Kabanov et al., *J. Controlled Release*, (1992) 22:141–158.

Chekhonin et al., *FEBS*, (1991) 287:149–152.

"Highlights of U.S. Patents," *Anti–Viral Agents Bulletin*, Dec. 1993.

Kabanov et al., *Sov. Sci. Rev. D. Physiochem. Biol.* (1992), 11:1–175.

Kabanov et al., "Increasing the Transforming Activity of Plasmid DNA...," Plenum Publishing Corporation (1989), pp. 133–136.

Levashov et al., "Chemical Modification of Proteins (Enzymes) with Water Insoluble Reagents" (1984), pp. 295–297.

Levashov et al., "Translocation of Waterproofed Proteins (Enzymes) into Lysosymes" (1985).

Kabanov et al, *Collect. Czech. Chem. Commun.* (1989), 54:835–837.

Kabanov et al.; *FEBS Letters* (1989), 250:238–240.

Kabanov et al., *Biol. Memb.* (1989), 2:1769–1785.

Kabanov et al., *Protein Engineering* (1989), 3:39–42.

Martinek et al., *Biochemica et Biophysica Acta* (1989), 981:161–172.

Kabanov et al., *Biomedical Science* (1990), 1:33–36.

Alakhov et al., *Biotechnology & Applied Biochemistry* (1990), 12:94–98.

Severin et al., *Advances in Enzyme Regulation* (1990), pp. 417–430.

Kabanov et al., *Biomedical Science* (1990), 1:63–68.

Melik–Nubarov et al., "Immunotherapeutic Prospects of Infectious Diseases," Masihi and Lange., Eds., Springer–Verleg, Berlin (1990), pp. 385–388.

Kabanov et al., *Collect. Czech. Chem. Commun.* (1990), 55:587–589.

Kabanov et al., International Symposium on Virology, Immunology and Society, Kozminov and Radavsky, Eds., UNESCO, Venice (1991), pp. 303–322.

Slepnev et al., *Bioconjugate Chem.* (1992), 3:273–274.

Kabanov, International Conference on Pharmaceutical Ingredients and Intermediates, Published by Manufacturing Chemists (1992), pp. 89–96.

Melik–Nubarov et al., *Biochem. Molec. Biol. Int'l.* (1993), 29:939–947.

Kabanov et al., *Bioconjugate Chemistry* (1993), 4:448–454.

Sukhishvili et al., *Polymer Science* (1993), 35:1602–1606.

Kabanov and Alakhov, Sixth International Symposium on Recent Advances in Drug Delivery Systems (1993), pp. 73–76.

Kabanov and Alakhov, *J. Controlled Release* (1994), 28:15–35.

Kabanov et al., *FEBS Letters* (1990), 259:327–330.

Kabanov et al., *Biopolymers* (1994), 34;1437–1443.

Kabanov et al., *Polymer Preprints* (1991), 32:592–593.

Jones et al., *Biconjugate Chem.* (1994), 5:390–399.

Wei, et al., *Bioconjugate Chem.* (1994), 5:464–478.

Jäsche et al., *Nucleic Acids Research* (1994), 22:4810–4817.

Kabanov et al., Polymeric Surfactant Micelles As Microcontainers..., *Journal of Neuroimmuno.* (Suppl 1): 130 (1991).

Chawla et al., "Aggregation of Insulin, Containing Surfactants, in Contact with Different Materials," Diabetes. vol. 34: 420–424 (1995).

Kabanov et al., "Interpolyelectrolyte and Block Ionomer Complexes for Gene Delivery: Physicochemical Aspects," Advanced Drug Delivery Reviews, Elsevier, vol. 30: 49–60 (1998).

Batrakova, "Effects of Pluronic Block Copolymers on Drug Absorption in Caco–2 Cell Monolayers," Pharmaceutical Research, vol. 15, No. 6, (1998).

Abstract, Database WPI Week 9519, Derwent Publ. Ltd. AN 95–144714 High Water Soluble Antitumour Adriamycin Agent Comprise Micellar Complex Block Copolymer Polyethyene Glycol Poly Amino acid.

Kataoka et al., "Block Copolymer Micelles As Vehicles for Drug Delivery," *Journal of Controlled Release*, vol. 24: 119–132 (1993).

Rekker, RF and AM ter Laak. On the reliability of calculated log p–values: Rekker, Hansch/Leo and Suzuki approack. Quant. Struct. Act. Relat. 12:152–157, 1993.

Cho, MJ and R Juliano. Macromolecular versus small–molecule therapeutics: drug discovery, development and clinical considerations. Trends in Biotechnology 14:153–158, 1996.

Mannhold, R. et al.. Comparative evaluation of the predictive power of calculation procedures for molecular lipophobicity. Journal of Pharmaceutical Sciences 84 (12): 1410–1419, 1995.

Cload, ST and A. Schepartz. Polyether tethered oligonucleotide probes. J. Am. Chem. Soc. 113:6324–6326, 1991.

Bennett, MR. et al. Inhibition of vascular smooth muscle cell proliferation in vitro and in vivo by c–myc antisense oligonucleotides. J. Clin. Invest. 93:820–828, 1994.

Haensler, J and FC Szoka. Polyamidoamine cascade polymers mediate efficient transfection of cells in culture. Bioconjugate Chem. 4:372–379, 1993.

* cited by examiner

POLYNUCLEOTIDE COMPOSITIONS

This is a continuation-in-part of Ser. No. 08/342,209, filed Nov. 18, 1994, now U.S. Pat. No. 5,656,611.

BACKGROUND OF THE INVENTION

The present invention relates to compositions of poly (nucleic acid) polymers such as RNA or DNA polymers and polycations that are associated, either covalently or noncovalently, with block copolymers of alkylethers. In a preferred embodiment, the poly(nucleic acids) will be complexed with a polycation. The nucleic acid is stabilized by the complex and, in the complex, has increased permeability across cell membranes. Accordingly, the complexes are well suited for use as vehicles for delivering nucleic acid into cells.

The use of antisense poly(nucleic acids) to treat genetic diseases, cell mutations (including cancer causing or enhancing mutations) and viral infections has gained widespread attention. This treatment tool is believed to operate, in one aspect, by binding to "sense" strands of mRNA encoding a protein believed to be involved in causing the disease state sought to be treated, thereby stopping or inhibiting the translation of the mRNA into the unwanted protein. In another aspect, genomic DNA is targeted for binding by the antisense polynucleotide (forming a triple helix), for instance, to inhibit transcription. See Helene, *Anti-Cancer Drug Design*, 6:569 (1991). Once the sequence of the mRNA sought to be bound is known, an antisense molecule can be designed that binds the sense strand by the Watson-Crick base-pairing rules, forming a duplex structure analogous to the DNA double helix. *Gene Regulation: Biology of Antisense RNA and DNA*, Erikson and lxzant, eds., Raven Press, New York, 1991; Helene, *Anti-Cancer Drug Design*, 6:569 (1991); Crooke, *Anti-Cancer Drug Design*, 6:609 (1991). A serious barrier to fully exploiting this technology is the problem of efficiently introducing into cells a sufficient number of antisense molecules to effectively interfere with the translation of the targeted mRNA or the function of DNA.

One method that has been employed to overcome this problem is to covalently modify the 5' or the 3' end of the antisense polynucleic acid molecule with hydrophobic substituents. These modified nucleic acids generally gain access to the cells interior with greater efficiency. See, for example, Kabanov et al., *FEBS Lett.*, 259:327 (1990); Boutorin et al., *FEBS Lett.*, 23:1382–1390, 1989; Shea et al, *Nucleic Acids Res.*, 18:3777–3783 (1990). Additionally, the phosphate backbone of the antisense molecules has been modified to remove the negative charge (see for example, Agris et al., *Biochemistry*, 25:6268 (1986); Cazenave and Helene in *Antisense Nucleic Acids and Proteins: Fundamentals and Applications*, Mol and Van der Krol, eds., p. 47 et seq., Marcel Dekker, New York, (1991) or the purine or pyrimidine bases have been modified (see, for example, *Antisense Nucleic Acids and Proteins: Fundamentals and Applications*, Mol and Van der Krol, eds., p. 47 et seq., Marcel Dekker, New York (1991); Milligan et al. in *Gene Therapy For Neoplastic Diseases*, Huber and Laso, eds., p. 228 et seq., New York Academy of Sciences, New York (1994). Other attempts to overcome the cell penetration barrier include incorporating the antisense poly(nucleic acid) sequence into an expression vector that can be inserted into the cell in low copy number, but which, when in the cell, can direct, the cellular machinery to synthesize more substantial amounts of antisense polynucleic molecules. See, for example, Farhood et al., *Ann. N.Y. Acad. Sci.*, 716:23 (1994). This strategy includes the use of recombinant viruses that have an expression site into which the antisense sequence has been incorporated. See, e.g., Boris-Lawrie and Temin, *Ann. N.Y. Acad. Sci.*, 716:59 (1994). Others have tried to increase membrane permeability by neutralizing the negative charges on antisense molecules or other nucleic acid molecules with polycations. See, e.g. Kabanov et al., *Soviet Scientific Reviews*, Vol. 11, Part 2 (1992); 30 Kabanov et al., *Bioconjugate Chemistry* 4:448 (1993); Wu and Wu, *Biochemistry*, 27:887–892 (1988); Behr et al., *Proc. Natl. Acad Sci U.S.A.* 86:6982–6986 (1989). There have been problems with systemically administering poylnucleotides due to rapid clearance degradation and low bioavailability. In some cases it would be desirable to target polynucleotide molecules to a specific site in the body to specific target cells. Also, due to poor or low transport across biological barriers (such as the blood-brain barrier) the transport of polynucleotides to targets across this barrier is decreased or impossible. Additionally, the problems with low oral or rectal bioavailability dramatically hinders the administration of such polynucleotides (including oligonucleotides).

Of course, antisense polynucleic acid molecules are not the only type of polynucleic acid molecules that can usefully be made more permeable to cellular membranes. To make recombinant protein expression systems, the expression-directing nucleic acid must be transported across the membrane and into the eukaryotic or prokaryotic cell that will produce the desired protein. For gene therapy, medical workers try to incorporate, into one or more cell types of an organism, a DNA vector capable of directing the synthesis of a protein missing from the cell or useful to the cell or organism when expressed in greater amounts. The methods for introducing DNA to cause a cell to produce a new protein, ribozyme or a greater amount of a protein or ribozyme are called "transfection" methods. See, generally, *Neoplastic Diseases*, Huber and Lazo, eds., New York Academy of Science, New York (1994); Feigner, *Adv. Drug Deliv. Rev.*, 5:163 (1990); McLachlin, et al., *Progr. Nucl. Acids Res. Mol. Biol.*, 38:91 (1990); Karlsson, S. *Blood*, 78:2481 (1991); Einerhand and Valerio, *Curr. Top. Microbiol. Immunol*, 177:217–235 (1992); Makdisi et al., *Prog. Liver Dis.*, 10:1 (1992); Litzinger and Huang, *Biochim. Biophys. Acta*, 11, 13:201 (1992); Morsy et al., *J.A.M.A.*, 270:2338 (1993); Dorudi et al., *British J. Surgery*, 80:566 (1993).

A number of the above-discussed methods of enhancing cell penetration by antisense nucleic acid are generally applicable methods of incorporating a variety of poly (nucleic acids) into cells. Other general methods include calcium phosphate precipitation of nucleic acid and incubation with the target cells (Graham and Van der Eb, *Virology*, 52:456, 1983), co-incubation of nucleic acid, DEAE-dextran and cells (Sompayrac and Danna, *Proc. Natl. Acad. Sci.*, 12:7575, 1981), electroporation of cells in the presence of nucleic acid (Pofter et al., *Proc. Natl. Acad. Sci.*, 81:7161–7165, 1984), incorporating nucleic acid into virus coats to create transfection vehicles (Gitman et al., *Proc. Natl. Acad. Sci. U.S.A.*, 82:7309–7313, 1985) and incubating cells with nucleic acid incorporated into liposomes (Wang and Huang, *Proc. Natl. Acad. Sci.*, 84:7851–7855, 1987).

Another problem in delivering nucleic acid to a cell is the extreme sensitivity of nucleic acids, particularly ribonucleic acids, to nuclease activity. This problem has been particularly germane to efforts to use ribonucleic acids as anti-sense oligonucleotides. Accordingly, methods of protecting nucleic acid from nuclease activity are desirable.

DETAILED DESCRIPTION OF THE INVENTION

The invention thus relates to compositions of poly(nucleic acid) polymers such as RNA or DNA polymers, and polycations that are associated (either covalently or noncovalently) with block copolymers of alkylethers.

Structure of Block Copolymers

Block copolymers are most simply defined as conjugates of at least two different polymer segments (Tirrel, M. In: *Interactions of Surfactants with Polymers and Proteins.* Goddard E. D. and Ananthapadmanabhan, K. P. (eds.), CRC Press, Boca Raton, Ann Arbor, London, Tokyo, pp. 59–122, 1992). Some block copolymer architectures are presented in FIG. 1.

The simplest block copolymer architecture contains two segments joined at their termini to give an A—B type diblock. Consequent conjugation of more than two segments by their termini yields A—B—A type triblock, A—B—A—B— type multiblock, or even multisegment A—B—C— architectures. If a main chain in the block copolymer can be defined in which one or several repeating units are linked to different polymer segments, then the copolymer has a graft architecture of, e.g., an $A(B)_n$ type. More complex architectures include for example $(AB)_n$ or $A_nB_m$ starblocks which have more than two polymer segments linked to a single center.

In accordance with the present invention, all of these architectures can be useful for polynucleotide delivery, provided that they contain (a) at least one polycationic segment that will bind polynucleotide and (b) at least one water soluble segment that will solubilize the complex formed between the block copolymer and polynucleotide.

Formulas XVIII–XXIII of the instant invention are diblocks and triblocks. At the same time, conjugation of polycation segments to the ends of polyether of formula XVII would yield starblocks (e.g., $(ABC)_4$ type). In addition, the polyspermine of examples 13–15 (below) are branched. Modification of such a polycation with poly (ethylene oxide) yields a mixture of grafted block copolymers and starblocks.

In one embodiment, the poly(nucleic acids) will be complexed with a polycation. The nucleic acid is stabilized by the complex and, in the complex, has increased permeability across cell membranes. Accordingly, the complexes are well suited for use as vehicles for delivering nucleic acid into cells.

In a preferred first embodiment, the block copolymer is selected from the group consisting of polymers of formulas:

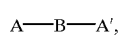   (I)

   (II)

   (III)

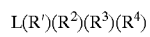   (IV)

L(R¹)(R²)(R³)(R⁴)

wherein A and A' are A-type linear polymeric segments, B and B' are B-type linear polymeric segments, and $R^1$, $R^2$, $R^3$ and $R^4$ are either block copolymers of formulas (I), (III) or (III) or hydrogen and L is a linking group, with the proviso that no more than two of $R^1$, $R^2$, $R^3$ or $R^4$ are hydrogen. In another preferred first embodiment of the invention, the polynucleotide composition shall further comprise a polycationic polymer comprising a plurality of cationic repeating units.

The composition provides an efficient vehicle for introducing polynucleotide into a cell. Accordingly, the invention also relates to a method of inserting poly(nucleic acid) into cells utilizing the first embodiment polynucleotide composition of the invention.

In a second embodiment, the invention provides a polynucleotide composition comprising:

(a) a polynucleotide or derivative thereof;

(b) a block copolymer having a polyether segment and a polycation segment, wherein the polyether segment comprises at least an A-type block, and the polycation segment comprises a plurality of cationic repeating units.

In a preferred second embodiment, the copolymer comprises a polymer of formulas:

   (V-a)

   (VI-a)

   (VII)

   (VIII-a)

   (V-b)

   (VI-b)

   (VIII-b)

   (VIII-c)

   (VIII-d)

wherein A, A' and B are as described above, wherein R and R' are polymeric segments comprising a plurality of cationic repeating units, and wherein each cationic repeating unit in a segment may be the same or different from another unit in the segment. The polymers of this embodiment can be termed "polyether/polycation" polymers. The R and R', blocks can be termed "R-type" polymeric segments or blocks.

The polynucleotide composition of the second embodiment provides an efficient vehicle for introducing the polynucleotide into a cell.

Accordingly, the invention also relates to a method of inserting poly(nucleic acid) into cells utilizing the second embodiment composition of the invention.

In a third embodiment, the invention provides a polynucleotide composition comprising a polynucleotide derivative comprising a polynucleotide segment and a polyether segment attached to one or both of the polynucleotide 5' and 3' ends, wherein the polyether comprises an A-type polyether segment.

In a preferred third embodiment, the derivative comprises a block copolymer of formulas:

   (IX-a)

   (X-a)

A—pN—A', (XI)

pN—A—B, (XII)

B—A—pN, (XIII)

A—B—A—pN, (XIII-a)

pN—A—B—A—pN (XIII-b)

A—pN—R, (IX-b)

R—A—pN, (IX-c)

A—R—pN, (IX-d)

pN—A—R, (X-b)

R—pN—A, (X-c)

pN—R—A (X-d)

(X-e)

B—A—B—pN, (X-f)

pN—B—A—B—pN wherein pN represents a polynucleotide having 5' to 3' orientation, and A, A' and B are polyether segments as described above. In another preferred third embodiment, the polynucleotide complex comprises a polycationic polymer.

Polymers of formulas (I), (II), (III) or (IV) can also be mixed with each other or can be mixed either additionally or alternatively with one or more of the polymers of formula (V-a or b), (VI-a or b), (VII-a or b) and (VIII-a or b) and/or with polynucleotide derivatives of formulas (IX-a,b,c or d), (X-a,b,c,d,e,or f), (XI), (XII) or (XIII) to provide an efficient vehicle for delivering poly(nucleic acid) to the interior of cells.

The polynucleotide composition of the third embodiment provides an efficient vehicle for introducing the polynucleotide into a cell. Accordingly, the invention also relates to a method of inserting poly(nucleic acid) into cells utilizing the third embodiment composition of the invention.

A fourth embodiment of the invention relates to a polyetherpolycation copolymer comprising a polymer, a polyether segment and a polycationic segment comprising a plurality of cationic repeating units of formula —NH—R$^0$—, wherein R$^0$ is a straight chain aliphatic group of 2 to 6 carbon atoms, which may be substituted, wherein said polyether segments comprise at least one of an A-type of B-type segment. In a preferred fourth embodiment, the polycation polymer comprises a polymer according to formulas:

B—A—R, (V)

A—R, (VI)

A—R—A', and (VII)

R—A—R', (VIII)

wherein A, A' and B are as described above, wherein R and R' are polymeric segments comprising a plurality of cationic repeating units of formula —NH—R$^0$—, wherein R$^0$ is a straight chain aliphatic group having from 2 to 6 carbon atoms, which may be substituted. Each —NH—R$^0$— repeating unit in an R-type segment can be the same or different from another —NH—R$^0$— repeating unit in the segment. A preferred fourth embodiment further comprises a polynucleotide or derivative.

In a fifth embodiment, the invention provides a polycationic polymer comprising a plurality of repeating units of formula:

$$[\text{—OR}^8\text{—OP(O)—}]$$
$$|$$
$$\text{NHR}^9\text{N(R}^{10})(R^{11})(R^{12})$$

where R$^8$ is:
(1) —(CH$_2$)$_n$—CH(R$^{13}$)—, wherein n is an integer from 0 to about 5, and R$^{13}$ is hydrogen, cycloalkyl having 3–8 carbon atoms, alkyl having 1–6 carbon atoms, or (CH$_2$)$_m$R$^{14}$, where m is an integer from 0 to about 12 and R$^{14}$ is a lipophilic substituent of 6 to 20 carbon atoms;
(2) a carbocyclic group having 3–8 ring carbon atoms, wherein the group can be for example, cycloalkyl or aromatic groups, and which can include alkyl having 1–6 carbon atoms, alkoxy having 1–6 carbon atoms, alkylamino having 1–6 carbon atoms, dialkylamino wherein each alkyl independently has 1–6 carbon atoms, amino, sulfonyl, hydroxy, carboxy, fluoro or chloro substituents; or
(3) a heterocyclic group, having 3–8 ring atoms, which can include heterocycloalkyl or heteroaromatic groups, which can include from 1 to 4 heteroatoms selected from the group consisting of oxygen, nitrogen, sulfur and mixtures thereto, and which can include alkyl having 1–6 carbon atoms, alkoxy having 1–6 carbon atoms, alkylamino having 1–6 carbon atoms, dialkylamino wherein each alkyl independently has 1–6 carbon atoms, amino, sulfonyl, hydroxy, carboxy, fluoro or chloro substituents.

R$^9$ is a straight chain aliphatic group of 1 to 12 carbon atoms, and R$^{10}$, R$^{11}$ and R$^{12}$ are independently hydrogen, an alkyl group of 1–4 carbon atoms. R$^9$ preferably comprises 2–10 carbon atoms, more preferably, 3–8. R$^{14}$ preferably includes an intercalating group, which is preferably an acrydine or ethydium bromide group. The number of such repeating units in the polymer is preferably between about 3 and 50, more preferably between about 5 and 20. This, polymer structure can be incorporated into other embodiments of the invention as an R-type segment or polycationic polymer. The ends of this polymer can be modified with a lipid substituent. The monomers that are used to synthesize polymers of this embodiment are suitable for use as the monomers fed to a DNA synthesizer, as described below. Thus, the polymer can be synthesized very specifically. Further, the additional incorporation of polynucleotide sequences, polyether blocks, and lipophilic substituents can be done using the advanced automation developed for polynucleotide syntheses. The fifth embodiment also encompasses this method of synthesizing a polycationic polymer.

In yet another embodiment, the invention relates to a polymer of a plurality of covalently bound polymer segments wherein said segments comprise (a) at least one polycation segment which segment is a cationic homopolymer, copolymer, or block copolymer comprising at least three aminoalkylene monomers, said monomers being selected from the group consisting of:

(i) at least one tertiary amino monomer of the formula:

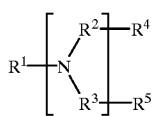
A and the quaternary salts of said tertiary amino monomer, and (ii) at least one secondary amino monomer of the formula:

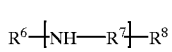
B and the acid addition and quaternary salts of said secondary amino monomer, in which:

$R^1$ is hydrogen, alkyl of 2 to 8 carbon atoms, an A monomer, or a B monomer; each of $R^2$ and $R^3$, taken independently of the other, is the same or different straight or branched chain alkanediyl group of the formula:

in which z has a value of from 2 to 8; $R^4$ is hydrogen satisfying one bond of the depicted geminally bonded carbon atom; and $R^5$ is hydrogen, alkyl of 2 to 8 carbon atoms, an A monomer, or a B monomer; $R^6$ is hydrogen, alkyl of 2 to 8 carbon atoms, an A monomer, or a B monomer; $R^7$ is a straight or branched chain alkanediyl group of the formula:

in which z has a value of from 2 to 8; and $R^8$ is hydrogen, alkyl of 2 to 8 carbon atoms, an A monomer, or a B monomer; and (b) at least one straight or branched chained polyether segment having from about 5 to about 400 monomeric units which is:
(i) a homopolymer of a first alkyleneoxy monomer —$OC_nH_{2n}$— or
(ii) a copolymer or block copolymer of said first alkyleneoxy monomer and a second different alkyleneoxy monomer —$OC_mH_{2m}$—, in which n has a value of 2 or 3 and m has a value of from 2 to 4.

The polycationic segments in the copolymers of the invention can be branched. For example, polyspermine-based copolymers are branched. The cationic segment of these copolymers was synthesized by condensation of 1,4-dibromobutane and N-(3-aminopropyl)-1,3-propanediamine. This reaction yields highly branched polymer products with primary, secondary, and tertiary amines.

An example of branched polycations are products of the condensation reactions between polyamines containing at least 2 nitrogen atoms and alkyl halides containing at least 2 halide atoms (including bromide or chloride). In particular, the branched polycations are produced as a result of polycondensation. An example of this reaction is the reaction between N-(3-aminiopropyl)-1,3-propanediamine and 1,4-dibromobutane, producing polyspermine.

Another example of a branched polycation is polyethyleneimine represented by the formula:

Additionally, cationic dendrimers, for example, polyamidoamines (Tomalia et al., Angew. Chem., Int. Ed. Engl. 1990, 29, 138) can be also used as polycation segments of block copolymers for gene delivery.

Included within the scope of the invention are compositions comprising these polymers and a suitable targeting molecule. Also included within the scope of the invention are compositions comprising polymer, a polynucleotide, and a surfactant. The invention also relates to copolymers comprising at least one polynucleotide segment and at least one polyether segment, said polyether segment comprising oxyethylene and oxypropylene.

The present compositions can be used in a variety of treatments. For example, the compositions can be used in Gene therapy including gene replacement or excision therapy, and gene addition therapy (B. Huber, In: Gene therapy for neoplastic diseases; B E Huber and J S Lazo Eds., The New York Academy of Sciences, NY, N.Y., 1994, pp. 6–11). Also, antisense therapy targets genes in the nucleus and/or cytoplasm of the cell, resulting in their inhibition (Stein and Cheng, Science 261:1004, 1993; De Mesmaeker et al. Acc. Chem. Res. 28:366, 1995). Aptamer nucleic acid drugs target both intra-and extracellular proteins, peptides and small molecules. See Ellington and Szostak, Nature (London), 346,818, 1990. Antigen nucleic acid compounds can be used to target duplex DNA in the nucleus. See Helene and Tolume, Biochim, Biophys. Acta 1049:99, 1990. Catalytic polynucleotides target mRNA in the nucleus and/or cytoplasm (Cech, Curr. Opp. Struct. Biol. 2:605, 1992).

Examples of genes to be replaced, inhibited and/or added include, but are not limited to, adenosine deaminase, tumor necrosis factor, cell growth factors, Factor IX, interferons (such as α-, β- and γ- interferon), interleukins (such interleukin 2,4, 6 and 12), HLA-B7, HSV-TK, CFTR, HIV -1, β-2, microglobulin, retroviral genes (such as gag, pol, env, tax, and rex), cytomegalovirus, herpes viral genes (such as herpes simplex virus type I and II genes ICP27/UL54, ICP22/US1, ICP/IE175, protein kinase and exonuclease/UL13, protein kinase/US3, ribonuclease reductase ICP6/UL39, immediate early (IE) mRNA IE3/IE 175/ICP4, 1E4/ICP22/US1, IE5/ICP47, IE110, DNA polymerase/UL30, UL13), human multidrug resistance genes (such as mdrl), oncogenes (such as H-c-ras, c-myb, c-myb, bcl-2, bcr/abl), tumor suppressor gene p53, human MHC genes (such as class 1 MHC), immunoglobulins (such as IgG, IgM, IgE, IgA), hemoglobin α- and β- chains, enzymes (such as carbonic anhydrase, triosephoshate isomerase, GTP-cyclhydrdolase I, phenylalanine hydrolase, sarcosine dehydrogenase, glucocerobrosidase, glucose-6-phosphste dehydrogenase), dysotrophin, fibronectin, apoliprotein E, cystic fibrosis transmembrane conductance protein, c-src protein, V(D)J recombination activating protein, immunogenes, peptide and protein antigens ("DNA vaccine") and the like.

Genetic diseases can also be treated by the instant compositions. Such diseases include, but are not limited to, rheumatoid arthritis, psoriasis, Crohn's disease, ulcerative colitis, α-thalassemia, β-thalassemia, carbonic anhydrase II deficiency syndrome, triosephosphate isomerase deficiency syndrome, tetrahydrobiopterindeficient hyperphenylalaniemia, classical phenylketonuria, muscular dystrophy such as Duchenne Muscular Dystrophy, hypersarkosinemia, adenomatous intestinal polyposis, adenosine deaminase deficiency, malignant melanoma, glucose-6-phosphste dehydrogenase deficiency syndrome, arteriosclerosis and hypercholesterolemia, Gaucher's disease, cystic fibrosis, osteopetrosis, increased spontaneous tumors, T and B cell immunodeficiency, high cholesterol, arthritis including chronic rheumatoid arthritis, glaucoma, alcoholism and the like.

The compositions can also be used to treat neoplastic diseases including, but not limited to, breast cancer (e.g., breast, pancreatic, gastric, prostate, colorectal, lung, ovarian), lymphomas (such as Hodgkin and non-Hodgkin lymphoma), melanoma and malignant melanoma, advanced cancer hemophilia B, renal cell carcinoma, gliblastoma, astrocytoma, gliomas, AML and CML and the like.

Additionally, the compositions can be used to treat (i) cardiovascular diseases including but not limited to stroke, cardiomyopathy associated with Duchenne Muscular Dystrophy, myocardial ischemia, restenosis and the like, (ii) infectious diseases such as Hepatitis, HIV infections and AIDS, Herpes, CMV and associated diseases such as CMV renitis, (iii) transplantation related disorders such as renal transplant rejection and the like, and (iv) are useful in vaccine therapies and immunization, including but not limited to melanoma vaccines, HIV vaccines, malaria, tuberculosis, and the like.

Target Cells

Cell targets can be ex vivo and/or in vivo, and include T and B lymphocytes, primary CML, tumor infiltrating lymphocytes, tumor cells, leukemic cells (such as HL-60, ML-3, KG-1 and the like), skin fibroblasts, myoblasts, cells of central nervous system including primary neurons, liver cells, carcinoma (such as Bladder carcinoma T24, human colorectal carcinoma Caco-2), melanoma, CD34+ lymphocytes, NK cells, macrophages, hemotopoetic cells, neuroblastona (such as LAN-5 and the like), gliomas, lymphomas (such as Burkitt lymphomas ST486), JD38), T-cell hybridomas, muscle cells such as primary smooth muscle, and the like.

Filed concurrently with the parent of this application (Nov. 18, 1994) was Ser. No. 08/342,079 entitled "POLYMER LINKED BIOLOGICAL AGENTS". The entire disclosure of that application is incorporated herein by reference.

The degree of polymerization of the hydrophilic (A-type) blocks or the hydrophobic (B-type) blocks of formulas (I)–(XIII) can preferably be between about 5 and about 400. More preferably, the degree of polymerization shall be between about 5 and about 200, still more preferably, between about 5 and about 80. The degree of polymerization of the R-type polycation blocks can preferably be between about 2 and about 300. More preferably, the degree of polymerization shall be between about 5 and about 180, still more preferably, between about 5 and about 60. The degree of polymerization of the polycationic polymer can preferably be between about 10 and about 10,000. More preferably, the degree of polymerization shall be between about 10 and about 1,000, still more preferably, between about 10 and about 100.

The repeating units that comprise the blocks, for A-type, B-type and R-type blocks, will generally have molecular weight between about 30 and about 500, preferably between about 30 and about 100, still more preferably between about 30 and about 60. Generally, in each of the A-type or B-type blocks, at least about 80% of the linkages between repeating units will be ether linkages, preferably, at least about 90% will be ether linkages, more preferably, at least about 95% will be ether linkages. Ether linkages, for the purposes of this application, encompass glycosidic linkages (i.e., sugar linkages). However, in one aspect, simple ether linkages are preferred.

The polynucleotide component (pN) of formulas (IX) through (XIII) will preferably comprise from about 5 to about 1,000,000 bases, more preferably about 5 to about 100,000 bases, yet more preferably about 10 to about 10,000 bases.

The polycationic polymers and the R-type blocks have several positively ionizable groups and a net positive charge at physiologic pH. The polyether/polycation polymers of formulas (V)–(VIII) can also serve as polycationic polymers. Preferably, the polycationic polymers and R-type blocks will have at least about 3 positive charges at physiologic pH, more preferably, at 25 least about 6, still more preferably, at least about 12. Also preferred, are polymers or blocks that, at physiologic pH, can present positive charges with about a spacing between the charges of about 3 Å to about 10 Å. The spacings established by aminopropylene repeating units, or by mixtures of aminopropylene and aminobutylene repeating units are most preferred.

Accordingly, for instance, polycationic segments that utilize a ($NHCH_2CH_2CH_2$) repeating unit, or a mixture of ($NHCH_2CH_2CH_2$) and ($NHCH_2CH_2CH_2CH_2$) repeating units, are preferred.

Polyether/polycation polymers of formulas (V)–(VIII) comprising a —NH—$R^0$— repeating unit are also preferred. $R^0$ is preferably an ethylene, propylene, butylene, or pentylene, which can be modified. In a preferred embodiment, in at least one of the repeating units, $R^0$ includes a DNA intercalating group such as an ethidium bromide group. Such intercalating groups can increase the affinity of the polymer for nucleic acid. Preferred substitutions on $R^0$ include alkyl of 1–6 carbons, hydroxy, hydroxyalkyl, wherein the alkyl has 1–6 carbon atoms, alkoxy having 1–6 carbon atoms, an alkyl carbonyl group having 2–7 carbon atoms, alkoxycarbonyl wherein the alkoxy has 1–6 carbon atoms, alkoxycarbonylalkyl wherein the alkoxy and alkyl each independently has 1–6 carbon atoms, alkylcarboxyalkyl wherein each alkyl group has 1–6 carbon atoms, aminoalkyl wherein the alkyl group has 1–6 carbon atoms, alkylamino or dialkylamino where each alkyl group independently has 1–6 carbon atoms, mono- or di-alkylaminoalkyl wherein each alkyl independently has 1–6 carbon atoms, chloro, chloroalkyl wherein the alkyl has from 1–6 carbon atoms, fluoro, fluoroalkyl wherein the alkyl has from 1–6 carbon atoms, cyano, or cyano alkyl wherein the alkyl has from 1–6 carbon atoms or a carboxyl group. More preferably, $R^0$ is propylene or butylene.

Polymers according to the first embodiment of the invention. are exemplified by the block copolymers having the formulas:

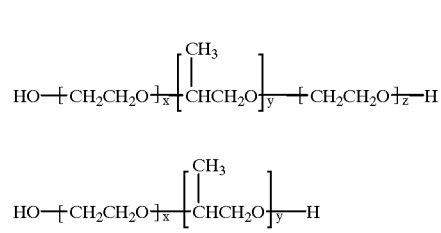
(XIV)

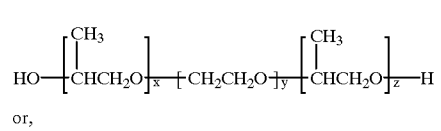
(XV)

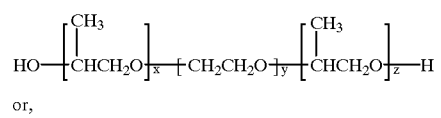
(XVI)

or,

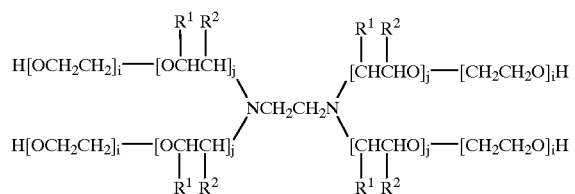
(XVII)

in which x, y, z, i and j have values from about 5 to about 400, preferably from about 5 to about 200, more preferably from about 5 to about 80, and wherein for each $R^1$, $R^2$ pair, one shall be hydrogen and the other shall be a methyl group.

Formulas (XIV) through (XVI) are oversimplified in that, in practice, the orientation of the isopropylene radicals within the B block will be random. This random orientation is indicated in formula (XVII), which is more complete. Such poly(oxyethylene)-poly(oxypropylene) compounds have been described by Santon, *Am. Perfumer Cosmet.* 72(4):54–58 (1958); Schmolka, Loc. cit. 82(7):25 (1967); Schick, *Non-ionic Surfactants*, pp. 300–371 (Dekker, N.Y., 1967). A number of such compounds are commercially available under such generic trade names as "poloxamers", "pluronics" and "synperonics." Pluronic polymers within the B—A—B formula are often referred to as "reversed" pluronics, "pluronic R" or "meroxapol". The "polyoxamine" polymer of formula (XVII) is available from BASF (Wyandotte, Mich.) under the tradename Tetronic™. The order of the polyoxyethylene and polyoxypropylene blocks represented in formula (XVII) can be reversed, creating Tetronic R™, also available from BASF. See, Schmolka, *J. Am. Oil Soc.*, 59:110 (1979). Polyoxypropylene-polyoxyethylene block copolymers can also be designed with hydrophilic blocks comprising a random mix of ethylene oxide and propylene oxide repeating units. To maintain the hydrophilic character of the block, ethylene oxide will predominate. Similarly, the hydrophobic block can be a mixture of ethylene oxide and propylene oxide repeating units. Such block copolymers are available from BASF under the tradename Pluradot™.

The diamine-linked pluronic of formula (XVII) can also be a member of the family of diamine-linked polyoxyethylene-polyoxypropylene polymers of formula:

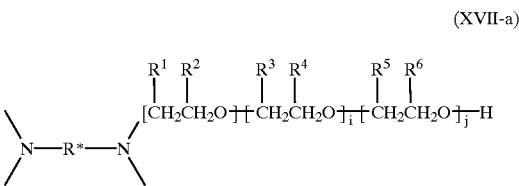
(XVII-a)

wherein the dashed lines represent symmetrical copies of the polyether extending off the second nitrogen, $R^*$ is an alkylene of 2 to 6 carbons, a cycloalkylene of 5 to 8 carbons or phenylene, for $R^1$ and $R^2$, either (a) both are hydrogen or (b) one is hydrogen and the other is methyl, for $R^3$ and $R^4$ either (a) both are hydrogen or (b) one is hydrogen and the other is methyl, if both of $R^3$ and $R^4$ are hydrogen, then one $R^5$ and $R^6$ is hydrogen and the other is methyl, and if one of $R^3$ and $R^4$ is methyl, then both of $R^5$ and $R^6$ are hydrogen.

Those of ordinary skill in the art will recognize, in light of the discussion herein, that even when the practice of the invention is confined for example, to poly(oxyethylene)-poly(oxypropylene) compounds, the above exemplary formulas are too confining. Thus, the units making up the first block need not consist solely of ethylene oxide. Similarly, not all of the B-type block need consist solely of propylene oxide units. Instead, the blocks can incorporate monomers other than those defined in formulas (XIV)–(XVII), so long as the parameters of the first embodiment are maintained. Thus, in the simplest of examples, at least one of the monomers in block A might be substituted with a side chain group as previously described.

In another aspect, the invention relates to a polynucleotide complex comprising a block copolymer at least one of formulas (I)–(XIII), wherein the A-type and B-type blocks are substantially made up of repeating units of formula —O—$R^9$, where $R^9$ is:

(1) —$(CH_2)_n$—$CH(R^6)$, wherein n is an integer from 0 to about 5 and $R^6$ is hydrogen, cycloalkyl having 3–8 carbon atoms, alkyl having 1–6 carbon atoms, phenyl, alkylphenyl wherein the alkyl has 1–6 carbon atoms, hydroxy, hydroxyalkyl, wherein the alkyl has 1–6 carbon atoms, alkoxy having 1–6 carbon atoms, an alkyl carbonyl group having 2–7 carbon atoms, alkoxycarbonyl, wherein the alkoxy has 1–6 carbon atoms, alkoxycarbonylalkyl, wherein the alkoxy and alkyl each independently has 1–6 carbon atoms, alkylcarboxyalkyl, wherein each alkyl group has 1–6 carbon atoms, aminoalkyl wherein the alkyl group has 1–6 carbon atoms, alkylamine or dialkylamino, wherein each alkyl independently has 1–6 carbon atoms, mono- or di-alkylaminoalkyl wherein each alkyl independently has 1–6 carbon atoms, chloro, chloroalkyl wherein the alkyl has from 1–6 carbon atoms, fluoro, fluoroalkyl wherein the alkyl has from 1–6 carbon atoms, cyano or cyano alkyl wherein the alkyl has from 1–6 carbon atoms or carboxyl; (2) a carbocyclic group having 3–8 ring carbon atoms, wherein the group can be for example, cycloalkyl or aromatic groups, and which can include alkyl having 1–6 carbon atoms, alkoxy having 1–6 carbon atoms, alkylamino having 1–6 carbon atoms, dialkylamino wherein each alkyl independently has 1–6 carbon atoms, amino, sulfonyl, hydroxy, carboxy, fluoro or chloro substitutions, or (3) a heterocyclic group, having 3–8 ring atoms, which can include heterocycloalkyl or heteroaromatic groups, which can include from 1–4 heteroatoms selected from the group consisting of oxygen, nitrogen, sulfur and mixtures thereto, and which can include alkyl having 1–6 carbon atoms, alkoxy having 1–6 carbon atoms, alkylamino having 1–6 carbon atoms, dialkylamino wherein each alkyl independently has 1–6 carbon atoms, amino, sulfonyl, hydroxy, carboxy, fluoro or chloro substitutions.

Preferably, n is an integer from 1 to 3. The carbocyclic or heterocyclic groups comprising $R^5$ preferably have from 4–7 ring atoms, more preferably 5–6. Heterocycles preferably include from 1–2 heteroatoms, more preferably, the heterocycles have one heteroatom. Preferably, the heterocycle is a carbohydrate or carbohydrate analog. Those of ordinary skill will recognize that the monomers required to make these polymers are synthetically available. In some cases, polymerization of the monomers will require the use of suitable protective groups, as will be recognized by those of ordinary skill in the art. Generally, the A- and B-type blocks are at least about 80% comprised of —$OR^5$— repeating units, more preferably at least about 90%, yet more preferably at least about 95%.

In another aspect, the invention relates to a polynucleotide complex comprising a block copolymer of one of formulas (I)–(XIII) wherein the A-type and B-type blocks consist essentially of repeating units of formula —O—$R^5$ wherein $R^7$ is a C to C alkyl group.

A wide variety of nucleic acid molecules can be the nucleic acid component of the composition. These include natural and synthetic DNA or RNA molecules and nucleic acid molecules that have been covalently modified (to incorporate groups including lipophilic groups, photo-induced crosslinking groups, alkylating groups, organometallic groups, intercalating groups, lipophilic groups, biotin, fluorescent and radioactive groups, and groups that modify the phosphate backbone). Such nucleic acid molecules can be, among other things, antisense nucleic acid molecules, gene-encoding DNA (usually including an appropriate promoter sequence), ribozymes, aptamers, anitgen nucleic acids, oligonucleotide α-anomers, ethylphosphotriester analogs, alkylphosphomates, phosphorothionate and phosphorodithionate oligonucleotides, and the like. In fact, the nucleic acid component can be any nucleic acid that can beneficially be transported into a cell with greater efficiency, or stabilized from degradative processes, or improved in its biodistribution after administration to an animal.

Examples of useful polymers pursuant to formulas (V)–(VIII) include the poly(oxyethylene)-poly-L-lysine) diblock copolymer of the following formula:

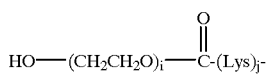

(XVIII)

wherein i is an integer of from about 5 to about 100, and j is an integer from about 4 to about 100. A second example is the poly(oxyethylene)-poly-(L-alanine-L-lysine) diblock copolymer of formula:

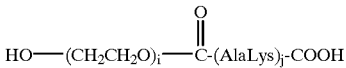

(XIX)

wherein i is an integer of from about 5 to about 100, and j is an integer from about 4 about 100. A third example is the poly(oxyethylene)-poly(propyleneimine/butyleneimine) diblock copolymer of the following formula:

(XX)

wherein i is an integer from about 5 about 200 and j is an integer from 1 to about 10. A fourth example is the poly(oxyethylene)-poly(N-ethyl-4-vinylpyridinium bromide) ("pOE-pEVP-Br") of formula:

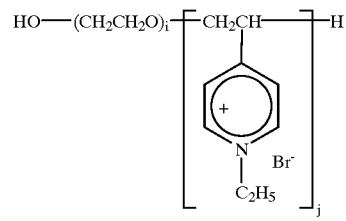

(XXI)

wherein i is an integer of from about 5 to about 100 and j is an integer of from about 10 to about 500. Still another example is the polymer of formula:

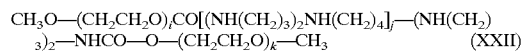

(XXII)

wherein i is an integer from about 10 to about 200, j is an integer from about 1 to about 8, and k is an integer from about 10 to about 200. Still another example is the polymer of formula:

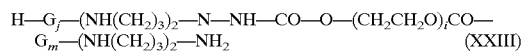

(XXIII)

wherein "G" comprises —$(NH(CH_2)_3)_3$—$CH_2NH_2$—, i and j are as defined for formula (XVIII), and m is an integer from about 1 to about 8.

The block copolymers utilized in the invention will typically, under certain circumstances, form micelles of from about 10 nm to about 100 nm in diameter. Micelles are supramolecular complexes of certain amphiphilic molecules that form in aqueous solutions due to microphase separation of the nonpolar portions of the amphiphiles. Micelles form when the concentration of the amphiphile reaches, for a given temperature, a critical micellar concentration ("CMC") that is characteristic of the amphiphile. Such micelles will generally include from about 10 to about 300 block copolymers. By varying the sizes of the hydrophilic and hydrophobic portions of the block copolymers, the tendency of the copolymers to form micelles at physiological conditions can be varied. The micelles have a dense core formed by the water insoluble repeating units of the B blocks and charge-neutralized nucleic acids, and a hydrophilic shell formed by the A blocks. The micelles have translational and rotational freedom in solution, and solutions containing the micelles have low viscosity similar to water. Micelle formation typically occurs at copolymer concentrations from about 0.001 to 5% (w/v). Generally, the concentration of polycationic polymers and polynucleic acid will be less than the concentration of copolymers in the polynucleotide compositions, preferably at least about 10-fold less, more preferably at least about 50-fold.

At high concentrations, some of the block copolymers utilized in the invention will form gels. These gels are viscous systems in which the translational and rotational freedom of the copolymer molecules is significantly constrained by a continuous network of interactions among copolymer molecules. In gels, microsegregation of the B block repeating units may or may not occur. To avoid the formation of gels, polymer concentrations (for both block copolymers and polyether/polycation polymers) will preferably be below about 15% (w/v), more preferably below about 10%, still more preferably below about 5%. In the first embodiment of the invention, it is more preferred that gels be avoided.

When the polynucleotide composition includes cationic components, the cations will associate with the phosphate groups of the polynucleotide, neutralizing the charge on the phosphate groups and rendering the polynucleotide component more hydrophobic. The neutralization is preferably supplied by cations on R-type polymeric segments or on polycationic polymers. However, the phosphate charge can also be neutralized by chemical modification or by association with a hydrophobic cations such as N-[1-(2,3-dioleyloxy)-N,N'-3-methylammonium chloride]. In aqueous solution, the charge neutralized polynucleotides are believed to participate in the formation of supramolecular, micelle-like particles, termed "polynucleotide complexes." The hydrophobic core or the complex comprises the charge neutralized polynucleotides and the B-type copolymer blocks. The hydrophilic shell comprises the A-type copolymer blocks. The size of the complex will generally vary from about 10 nm to about 100 nm in diameter. In some contexts, it is practical to isolate the complex from unincorporated components. This can be done, for instance, by gel filtration chromatography.

The ratio of the components of the polynucleotide composition is an important factor in optimizing the effective transmembrane permeability of the polynucleotides in the composition. This ratio can be identified as ratio Ø, which is the ratio of positively charged groups to negatively charged groups in the composition at physiological pH. If Ø<1, the complex contains non-neutralized phosphate from the polynucleotide. The portions of the polynucleotides adjacent to the non-neutralized charges are believed to be a part of the shell of a polynucleotide complex. Correspondingly, if Ø>1, the polycationic polymer or R-type segment will have non-neutralized charges, and the un-neutralized portions will fold so that they form a part of the shell of the complex. Generally, Ø will vary from about 0 (where there are no cationic groups) to about 100, preferably Ø will range between about 0.01 and about 50, more preferably, between about 0.1 and about 20. Ø can be varied to increase the efficiency of transmembrane transport and, when the composition comprises polynucleotide complexes, to increase the stability of the complex. Variations in Ø can also affect the biodistribution of the complex after administration to an animal. The optimal Ø will depend on, among other things, (1) the context in which the polynucleotide composition is being used, (2) the specific polymers and oligonucleotides being used, (3) the cells or tissues targeted, and (4) the mode of administration.

It will in some circumstances be desirable to incorporate, by noncovalent association, to targeting molecules. See for example, Kabanov et al., *J. Controlled Release,* 22:141 (1992), the contents of which are hereby incorporated by reference. The targeting molecules that can be associated with the composition typically have a targeting group having affinity for a cellular site and a hydrophobic group. The targeting molecule will spontaneously associate with the polynucleotide complex and be "anchored" thereto through the hydrophobic group. These targeting adducts will typically comprise about 10% or less of the copolymers in a composition.

In the targeting molecule, the hydrophobic group can be, among other things, a lipid group such as a fatty acyl group. Alternately, it can be a block copolymer or another natural synthetic polymer. The targeting group of the targeting molecule will frequently comprise an antibody, typically with specificity for a certain cell surface antigen. It could also be, for instance, a hormone having a specific interaction with a cell surface receptor, or a drug having a cell surface receptor. For example, glycolipids could serve to target a polysaccharide receptor. It should be noted that the targeting molecule can be attached to any of the polymer blocks identified herein, including R-type polymeric blocks and to the polycationic polymers. For instance, the targeting molecule can be covalently attached to the free-terminal groups of the polyether segment of the block copolymer of the invention. Such targeting molecules can be covalently attached to the—OH end group of the polymers of the formulas XVIII, XIX, XX, and XXI, and the —NH$_2$ end group of the polymers of formulas XVIII (preferably the ε-amino group of the terminal lysyl residue), XX or XXIII, or the —COOH end group of the polymers of formulas XVIII and XIX. Targeting molecules can be used to facilitate intracellular transport of the polynucleotide composition, for instance transport to the nucleus, by using, for example, fusogenic peptides as targeting molecules described by Soukchareun et al., *Bioconjugate Chem.,* 6, 43, 1995 or Arar et al., *Bioconjugate Chem.,* 6, 43, 1995, caryotypic peptides, or other biospecific groups providing site-directed transport into a cell (in particular, exit from endosomic compartments into cytoplasm, or delivery to the nucleus).

The polynucleotide component of the compositions of the invention can be any polynucleotide, but preferably a polynucleotide with at least about 3 bases, more preferably at least about 5 bases. Still more preferred are at least 10 bases. Included among the suitable polynucleotides are viral genomes and viruses (including the lipid or protein viral coat). This includes viral vectors including, but not limited to, retroviruses, adenoviruses, herpes-virus, or Pox-virus. Other suitable viral vectors for use with the present invention will be obvious to those skilled in the art. The terms "poly(nucleic acid)" and "polynucleotide" are used interchangeably herein. An oligonucleotide is a polynucleotide, as are DNA and RNA.

A polynucleotide derivative is a polynucleotide having one or more moieties (i) wherein the moieties are cleaved, inactivated or otherwise transformed so that the resulting material can function as a polynucleotide, or (ii) wherein the moiety does not prevent the derivative from functioning as a polynucleotide.

For polyethylene oxide-polypropylene oxide copolymers, the hydrophilic/hydrophobic properties, and micelle form ing properties of a block copolymer are, to a certain degree, related to the value of the ratio, n. The ratio, n, is defined as:

$$n=(|B|/|A|)\times(b/a)=(|B|/|A|)\times 1.32$$

where |B| and |A| are the number of repeating units. in the hydrophobic and hydrophilic blocks of the copolymer, respectively, and b and a are the molecular weights for the respective repeating units. The value of n will typically be between about 0.2 and about 9.0, more preferably, between about 0.2 and about 1.5. Where mixtures of block copolymers are used, n will be the weighted average of n for each contributing copolymers, with the averaging based on the weight portions of the component copolymers. When copolymers other than polyethylene oxide-polypropylene oxide copolymers are used, similar approaches can be developed to relate the hydrophobic/hydrophilic properties of one member of the class of polymers to the properties of another member of the class.

Surfactant-Containing Polynucleotide Compositions

The invention also includes compositions of polynucleotide, cationic copolymer, and a suitable surfactant. The surfactant, should be (i) cationic (including those used in various transfection cocktails), (ii) nonionic (e.g., Pluronic or Tetronic), or (iii) zwitterionic (including betains and phospholipids). These surfactants increase solubility of the complex and increase biological activity of the compositions.

Cationic surfactants include but are not limited to primary amines, secondary amines, tertiary amines (e.g., N,N',N'-polyoxyethylene(10)-N-tallow-1,3-diaminopropane), quaternary amine salts (e.g., dodecyltrimethylammonium bromide, hexadecyltrimethylammonium bromide, mixed alkyl-trimethylammonium bromide, tetradecyltrmethylammonium bromide, benzalkonium chloride, benzethonium chloride, benzyldimethyldodecylammonium chloride, benzyl-dimethylhexadecylammonium chloride, benzyltrimethylammonium methoxide, cetyldimethyl-ethylammonium bromide, dimethyldioctadecyl ammonium bromide, methylbenzethonium chloride, decamethonium chloride, methyl mixed trialkyl ammonium chloride, methyl trioctylammonium chloride), N,N-dimethyl-N-[2-(2-methyl-4-(1,1,3,3-tetramethylbutyl)-phenoxy]ethoxy)ethyl]-benzenemethanaminium chloride (DEBDA), dialkyldimethylammonium salts, N-[1-(2,3-dioleyloxy)-propyl]-N,N,N,-trimethylammonium chloride, 1,2-diacyl-3-(trimethylammonio)propane (acyl group=dimyristoyl, dipalmitoyl, distearoyl, dioleoyl), 1,2-diacyl-3-(dimethylammonio)propane (acyl group=dimyristoyl, dipalmitoyl, distearoyl, dioleoyl), 1,2-dioleoyl-3-(4'-trimethylammonio) butanoyl-sn-glycerol, 1,2-dioleoyl-3-succinyl-sn-glycerol choline ester, cholesteryl (4'-trimethylammonio) butanoate), N-alkyl pyridinium salts (e.g. cetylpyridinium bromide and cetylpyridinium chloride), N-alkylpiperidinium salts, dicationic bolaform electrolytes ($C_{12}Me_6$; $C_{12}Bu_6$), dialkyl-glycetylphosphoryl lysolecithin, L-α dioleoyl phosphatidylethanolamine), cholesterol hemisuccinate choline ester, lipopolyamines (e.g., dioctadecylamidoglycylspermine (DOGS), dipalmitoyl phosphatidylethanolamidospermine (DPPES), lipopoly-L (or D)-lysine (LPLL, LPDL), poly(L (or D)-lysine conjugated to N-glutarylphosphatidylethanolamine, didodecyl glutamate ester with pendant amino group ($C_{12}GluPhC_nN^+$), ditetradecyl glutamate ester with pendant amino group ($C_{14}GluC_nN^+$), cationic derivatives of cholesterol (e.g., cholesteryl-3β-oxysuccin-amidoethylenetrimethylammonium salt, cholesteryl-3β-oxysuccinamidoethylenedimethylamine, cholesteryl-3β-carboxyamidoethylenetrimethylammonium salt, cholesteryl-3β-carboxyamido-ethylenedimethylamine, 3β[N-(N',N'-dimethylaminoetane-carbomoil]cholesterol).

Non-ionic surfactants include but are not limited to n-Alkylphenyl polyoxyethylene ether, n-alkyl polyoxyethylene ethers (e.g., Tritons™), sorbitan esters (e.g., Spans™), polyglycol ether surfactants (Tergitol™), polyoxyethylene-sorbitan (e.g., Tweens™), polysorbates, poly-oxyethylated glycol monoethers (e.g., Brij™, polyoxylethylene 9 lauryl ether, polyoxylethylene 10 ether, polyoxylethylene 10 tridecyl ether), lubrol, copolymers of ethylene oxide and propylene oxide (e.g., Pluronic™, Pluronic R™, Teronic™, Pluradot™), alkyl aryl polyether alcohol (Tyloxapol™), perfluoroalkyl polyoxylated amides, N,N-bis[3-D-gluconamidopropyl]cholamide, decanoyl-N-methylglucamide, n-decyl α-D-glucopyranozide, n-decyl β-D-glucopyranozide, n-decyl β-D-maltopyranozide, n-dodecyl β-D-glucopyranozide, n-undecyl β-D-glucopyranozide, n-heptyl β-D-glucopyranozide, n-heptyl β-D-thioglucopyranozide, n-hexyl β-D-glucopyranozide, n-nonanoyl β-D-glucopyranozide 1-monooleyl-rac-glycerol, nonanoyl-N-methylglucamide, n-dodecyl α-D-maltoside, n-dodecyl β-D-maltoside, N,N-bis[3-gluconamidepropyl]deoxycholamide, diethylene glycol monopentyl ether, digitonin, heptanoyl-N-methylglucamide, heptanoyl-N-methylglucamide, octanoyl-N-methylglucamide, n-octyl β-D-glucopyranozide, n-octyl β-D-glucopyranozide, n-octyl β-D-thiogalactopyranozide, n-octyl β-D-thioglucopyranozide.

Zwitterionic surfactants include but are not limited to betaine ($R_1R_2R_3N^+R'CO_2^-$, where $R_1R_2R_3R'$ are hydrocarbon chains and $R_1$ is the longest one), sulfobetaine ($R_1R_2R_3N^+R'SO_3^-$), phospholipids (e.g., dialkyl phosphatidylcholine), 3-[(3-cholamidopropyl)-dimethylammonio]-2-hydroxy-1-propanesulfonate, 3-[(3-cholamidopropyl)-dimethylammonio]-1-propanesulfonate, N-decyl-N,N-dimethyl-3-ammonio-1-propanesulfonate, N-dodecyl-N,N-dimethyl-3-ammonio- 1-propane-sulfonate, N-hexadecyl-N,N-dimethyl-3-ammonio-1-propanesulfonate, N-octadecyl-N,N-dimethyl-3-ammonio-1-propanesulfonate, N-octyl-N,N-dimethyl-3-ammonio-1-propanesulfonate, N-tetradecyl-N,N-dimethyl-3-ammonio-1-propanesulfonate, and dialkyl phosphatitidylethanolamine.

The polynucleotide compositions of the invention can be administered orally, topically, rectally, vaginally, by pulmonary route by use of an aerosol, or parenterally, i.e. intramuscularly, subcutaneously, intraperitoneallly or intravenously. The polynucleotide compositions can be administered alone, or it can be combined with a pharmaceutically-acceptable carrier or excipient according to standard pharmaceutical practice. For the oral mode of administration, the polynucleotide compositions can be used in the form of tablets, capsules, lozenges, troches, powders, syrups, elixirs, aqueous solutions and suspensions, and the like. In the case of tablets, carriers that can be used include lactose, sodium citrate and salts of phosphoric acid. Various disintegrants such as starch, and lubricating agents such as magnesium stearate, sodium lauryl sulfate and talc, are commonly used in tablets. For oral administration in capsule form, useful diluents are lactose and high molecular weight polyethylene glycols. When aqueous suspensions are required for oral use, the polynucleotide compositions can be combined with emulsifying and suspending agents. If desired, certain sweetening and/or flavoring agents can be added. For parenteral administration, sterile solutions of the conjugate are usually prepared, and the pH of the solutions are suitably adjusted and buffered. For intravenous use, the total concentration of solutes should be controlled to render the preparation isotonic. For ocular administration, ointments or droppable liquids may be delivered by ocular delivery systems known to the art such as applicators or eye droppers. Such compositions can include mucomimetics such as hyaluronic acid, chondroitin sulfate, hydroxypropyl methylcellulose or poly(vinyl alcohol), preservatives such as sorbic acid, EDTA or benzylchronium chloride, and the usual quantities of diluents and/or carriers. For pulmonary administration, diluents and/or carriers will be selected to be appropriate to allow the formation of an aerosol.

The following examples will serve to further typify the nature of the invention but should not be construed as a limitation on the scope thereof, which is defined solely by the appended claims.

EXAMPLE 1

Transfection Efficiencies—First Embodiment Complex

This experiment sought to introduce plasmid pβ-Gal into NIH 3T3 cells, a mouse mammary tumor cell line. Plasmid pβ-Gal comprises plasmid pUC19 (available from the Institute of Gene Biology, Russian Academy of Sciences) into which a hybrid of a eukaryotic transcription unit and a E. coli β-galactosidase has been incorporated. With this plasmid, the efficiency of cell uptake can be measured by measuring β-galactosidase activity extractable from the treated cells. The copolymer utilized was a triblock copolymer of formula (XIV) wherein x plus z was 51 and y was 39 (hereinafter "Pluronic A"). The polycation utilized was poly(N-ethyl-4-vinylpyridinium bromide) ("pEVP-Br"). A 10, µg/ml solution of pβ-Gal (predominantly supercoiled) was prepared in a solution of PBS containing 10 mg/ml of pluronic A and 45, µg/ml of pEVP-Br. These amounts were calculated to provide a ratio of polycation basic groups to plasmid phosphate groups of about 10. The ratio of pluronic A to DNA was about $10^4$. This stock preparation was filter sterilized and a portion was diluted ten fold with serum-free Dulbecco's Modified Eagle's Medium ("DMEM"), so that the concentration of pβ-Gal was 1 µg/ml. This solution was the "Pluronic A transfecting medium."

The NIH 3T3 cells were grown in monolayer culture at 37° C. under 5% $CO_2$, utilizing a DMEM medium containing 2 mM glutamine and 10% fetal calf serum ("FCS"). Cells were grown in monolayer culture were scraped and prepared for the transaction process by washing three times with fresh medium.

Aliquots of washed cells that were to be transformed by the method of the invention were suspended at a concentration of $10^6$ cells/ml in Pluronic A transfecting medium. The suspended cells were incubated for 2 hours at 37° C. and under 5% $CO_2$. The cells were then washed with fresh medium and re-plated.

Aliquots of cells that were to be transfected by calcium phosphate precipitation were transfected as recommended by Promega of Madison, Wis., in their manuscript *Profection Mammalian Transfeclion Systems*, Technical Manual, 1990. Specifically, pβ-Gal was mixed with 0.25M $CaCl_2$. The mixture was mixed with an equal volume of 2×HBS (Hanks Buffer Salt, available from GIBCO, Grand Island, N.Y.) to create a mixture containing 1 µg/mL pβ-Gal. The opaque mixture was incubated at room temperature for 10 minutes and then applied to the cells. The suspended cells were incubated for 2 hours at 37° C. and under 5% $CO_2$. The cells were then washed with fresh medium and re-plated.

The repeated cells were incubated for 48 hours in DMEM medium containing 10% FCS. During the incubation, the medium was replaced with fresh medium at 16 hours. After the 48 hour incubation, the cells for each incubation were collected by scrapping, washed with PBS, and resuspended in 100 µl of 0.2 M Tris-HCL (pH 7.4). The cells were lysed with several freeze/thaw cycles, and centrifuged at an excess of 6,000 x/g. 50 µl of supernatant was removed from each lysate tube and mixed with 50 µl of a solution of 0.1 mM 4-methyl-umbelliferril-β-D-galactopiraniside (the substrate), 0.1 M sodium phosphate (pH 7.4). Each mixture was incubated for 20 min. at 37° C. to allow any 9-galactosidase present to act on the substrate. 50 µl of 0.4 M glycine, pH 10.5, was added to terminate the β-galactosidase reaction. β-galactosidase activity was indicated by the presence of methylbelliferon, which can be measured by fluorescence spectroscopy ($\lambda_{ex}$=365 nm, $\lambda$=450 nm). The results were as follows:

| Treatment | Relative Enzyme Activity ± SEM (n = 4) |
|---|---|
| Pluronic A | 320 ± 42 |
| Calcium Phosphate Precipitation | 17 ± 5 |

EXAMPLE 2

Transfection Efficiencies—First Embodiment Complex

In these experiments, transfection efficiencies with MDCK cells (derived from canine kidney) were examined. Again, pβ-Gal was the indicator polynucleotide. The polycation component of the polynucleotide comprised a copolymer of N-ethyl-4-vinylpyridinium bromide and N-cetyl-4-vinylpyridinium bromide, the monomers incorporated in a molar ratio of 97:3, respectively (hereinafter "pEVP-co-pCVP-Br"). The block copolymer comprised a triblock copolymer of formula (XIV) wherein x+z was 18 and y was 23 (hereinafter "Pluronic B"). A Pluronic B transfecting solution of 1 µg/ml pβ-Gal, 3 µg/ml PEVPco-pCVP-Br, and 1% (w/v) Pluronic B was prepared in Example 1. The ratio of polycation basic groups to nucleotide Phosphates was about 7. The weight ratio of Pluronic B to pβ-Gal was about $5 \times 10^3$.

MDCK cells were plated at 8–$10^5$ cells per plate onto 90 mm plates and incubated overnight under serum-containing growth medium. The serum containing medium was then replaced with serum-free medium, and the cells were incubated at 37° C., under 5% $CO^2$ for 24 hours. For the cells to be treated with polynucleotide complex, the medium was then replaced with 5 ml Pluronic B transfecting solution. The cells were incubated, with gentle rocking, at 37° C., under 5% $CO_2$ In control experiments, cells were transfected with polynucleotide complex, the medium was then replaced with 5 ml Pluronic B transfecting solution. The cells were incubated, with gentle rocking, at 37° C., under 5% $CO_2$, for 2 hours. In control experiments, cells were transfected using the calcium phosphate procedure as described above (except that plated cells, not suspended cells, were transfected).

After treatment with Pluronic B transfecting solution or calcium phosphate, the cells were washed 5–6 times with fresh medium. They were then incubated in DMEM containing 10% FCS for 48 hours at 37° C., under 5% $CO_2$. After the first 16 hours of this incubation, the medium was replaced. After the incubation, the cells were washed with PBS, released from their plates by trypsinization, and again washed with PBS. β-Galactosidase was measured as described for Example 1. The results were as follows:

| Treatment | Relative β-galactosidase activity ± SEM (n = 4) |
|---|---|
| Pluronic B | 910 ± 45 |
| Calcium Phosphate Precipitation | 81 ± 17 |

EXAMPLE 3

Transfection Experiments—First Embodiment Complex

In these experiments, transfection efficiencies with Chinese hamster ovary (CHO) cells were examined. The polynucleotic component of the polynucleotic complex was pβ-Gal. The polycation component comprised pEVPBr. The block copolymer comprised an octablock copolymer formula (XVII), wherein i was equal to 10 and j was equal to 12 (hereinafter "Pluronic C" available from BASF). A Pluronic C transfecting solution of 1 μg/ml pβ-Gal, 4 μg/ml pEVP-Br, and 1% (w/v) Pluronic C was prepared as in Example 1. The ratio of basic groups to nucleotide phosphates was 10. The weight ratio of Pluronic C to pβ-Gal was $10^3$. The transfection protocol was the same as that used in Example 2. The results were as follows:

| Treatment | Relative β-galactosidase activity ± SEM (n = 4) |
|---|---|
| Pluronic B | 910 ± 45 |
| Calcium Phosphate Precipitation | 81 ± 17 |

EXAMPLE 4

Bacterial Transformation—Second Embodiment Complex

In these experiments, transformation efficiencies using the MC5 strain of *Bacillus subtilis* were examined. The polynucleotide component of the polynucleotide complex was plasmid pBC16, a plasmid encoding tetracycline resistance. A block copolymer according to formula (VI) was used. In particular, the block copolymer was a poly(oxyethylene)-oly((N-ethyl-4-vinylpyridinium bromide) of formula (XXI), wherein i was 44, and j was 20. A stock solution of second embodiment polynucleotide complex was prepared consistent with the transfection solutions described above. The ratio of copolymer basic groups to DNA phosphates in the solution was 0.2. Bacteria were suspended in Spizizen 11, a transformation media (see, Spizizen, F.N.A.S., U.S.A. 44:1072 (1958)), and aliquots of cells were incubated in varying concentrations of either polynucleotide complex or free pBC16. The cells were incubated with complex or free DNA for one hour at 37° C. Following the incubation, the cells were plated onto agar media containing 10 mg/ml tetracycline. The results, measured by the number of tetracycline-resistant colonies produced under each of the experimental conditions, were as follows:

| DNA concentration (ng/ml) | Transformation($10^6$ clones/ng DNA) | |
|---|---|---|
| | Polynucleotide Complex | Free Polynucleotide |
| 5 | 300 (±15) | 0 |
| 10 | 450 (±22) | 3 (±1) |
| 20 | 400 (±26) | 3 (±4) |
| 50 | 220 (±17) | 20 (±5) |

EXAMPLE 5

Protection from Nuclease

For this example, a complex of plasmid pTZ19 and a diblock copolymer of formula (XXI) (poly(oxyethylene)-poly((N-ethyl-4vinylpyridinium bromide), wherein i was 44 and j was 20) was formed. The solution of polynucleotide complex dissolved in PBS contained about 4 μg/ml of plasmid and 20 μg/ml of diblock copolymer. These amounts resulted in a ratio of base groups in the polycation block to DNA phosphate groups of 5. For control incubations, an equivalent amount of free plasmid was dissolved in buffer. PVUII nuclease was added to solution samples containing free DNA or polynucleotide complex, and the amount of undigested, circular plasmid DNA, after various digestion times, was determined by electrophoresis in a polyacrylamide gel. See Kabanov el al., *Biopolymers,* 31:1437–1443 (1991). The results were as follows:

| | Circular DNA (% of initial) | |
|---|---|---|
| Time of Incubation | Complex | Free DNA |
| 0 | 100 | 100 |
| 5 | 100 | 20 |
| 10 | 100 | 8 |
| 30 | 100 | 4 |
| 60 | 100 | 1 |
| 180 | 100 | 0 |
| 600 | 100 | 0 |

EXAMPLE 6

Oligonucleotide Stabilization

For this example, a complex containing an oligonucleotide complementary to the transcription initiation site of the HIV-1 tat gene ("anti-tat", comprising GGCTCCATTTCTTGCTC) was prepared using the diblock copolymer of formula (XIX) (polyoxyethylene-poly(L-alanine-L-lysine), wherein i is 44 and j is 8). The oligonucleotide complex was prepared in PBS Buffer (pH 7.0) at a concentration of 0.75 $OD_{260}$/μl oligonucleotide. The ratio of polycation imino and amino groups to polynucleotide phosphate groups was about 50. The mixture was incubated for one hour at room temperature to allow for the formation of the complex. Then, the complex was purified by gel filtration chromatography on Sephadex G-25 using 0.05M NaCl as the eluent. The resulting solution of complex exhibited a concentration of 0.11 $OD_{260}$/μl of oligonucleotide. A comparable solution of uncomplex oligonucleotide was prepared. An aliquot of murine blood plasma (10 μl) was mixed with an equal volume of oligonucleotide complex solution or a solution of free oligonucleotide. Samples were incubated at 37° C. for various time periods. To stop the reaction of the oligonucleotides with enzymes in the plasma, the samples were diluted with water and extracted with a water-saturated mixture of phenol:chloroform (1:1). The aqueous phase of the extraction was isolated, and the oligonucleotide therein was precipitated with 3% lithium Perchlorate. The precipitate was washed with acetone, and then dissolved in 100 µl of water. The presence of undergraded oligonucleotide was determined by high performance liquid chromatography using a $C_{18}$-Silasorb column (4×90 mm, Gilson, France) and a gradient of acetonitrile in 0.05 M triethylammoniumacetate(pH 7.0) as the eluent. The results were as follows:

| Time of | Undergraded oligonucleotide (%) | |
|---|---|---|
| Incubation | Complex | Free Oligo |
| 0 | 100 | 100 |
| 3 hours | 88 | 28 |
| 6 hours | 70 | 17 |
| 24 hours | 36 | 0 |

EXAMPLE 7

Oligonucleotide Stabilization

This example examined the stability of the oligonucleotide described in Example 6, when complexed with a diblock copolymer of formula (XX) (polyoxyethylene-polypropyleneimine/butyleneimine, wherein i is 44 and j is 4–8) was examined. The same methodologies that were applied in Example 6 were applied for this example, except that the oligonucleotide concentration was about 0.13 $OD_{260}$/µl. The results were as follows:

| Time of | Undergraded oligonucleotide (%) | |
|---|---|---|
| Incubation | Complex | Free Oligo |
| 0 | 100 | 100 |
| 3 hours | 70 | 28 |
| 6 hours | 57 | 17 |
| 24 hours | 28 | 0 |

EXAMPLE 8

Antisense Cell Incorporation Efficiencies

This experiment examined the effectiveness of "anti-MDR", an antisense molecule comprising a 17-chain oligonucleotide of sequence CCTTCAAGATCCATCCC complementary to positions 422–438 of the mRNA encoding the MDR1 gene product, in reversing multi-drug resistance in SKVLB cells. SKVLB cells are multi-drug resistant cells derived from a ovarian cancer cell line. The MDR1 gene has been identified as responsible for the multi-drug resistance in SKVLB cells. Endicott and Ling, *Ann. Rev. Biochem.*, 58:137 (1989). In particular, the efficiency of the anti-MDR oligonucleotide in the polynucleotide complex of the invention and when in the free state was compared. As controls, the free and completed form of the anti-tat oligonucleotide described above were also used. The polynucleotide complexes were formed with the diblock copolymer of formula (XX) (polyoxyethylenepolypropyleneimine/butyleneimine, where i was 44 and j was 9–10). The; complexes were prepared by the procedures described in Example 6. The oligonucleotide concentration in the complex or in the free state was 0.17 $OD_{260}$/µl. The copolymer was present in the concentration sufficient to define a ratio of polycation block imino and amino groups to oligonucleotide phosphate groups of 10.

The SKVLB cells were incubated for 3 days at 37° C. under 5% $CO_2$ in the presence of free or completed oligonucleotide (at a concentration of 20 µM based on oligonucleotide content). Fresh media including free or completed oligonucleotide was added every 12 hours.

The daunomycin cytotoxicity ($IC_{50}$) with respect to the cells treated as described above was measured using the method of Alley et. al., *Cancer Res.*, 48:589–601. The results were as follows:

| Treatment of Cells | Daunomycin $IC_{50}$ (ng/ml) (n = 4) |
|---|---|
| Control (untreated cells) | 8.0 |
| Anti-MDR Complex | 0.3 |
| Anti-tat Complex | 8.2 |
| Free Anti-MDR | 2.1 |
| Free Anti-tat | 7.9 |

EXAMPLE 9

Antisense Oligonucleotide Designed to Inhibit Herpes Virus

This experiment utilized a 12-chain oligonucleoticle, which had been covalently modified at its 5' end with undecylphosphate substituent and at is 3' end with a acridine group, was used. This oligonucleotide modification has been described by Cho-Chung et. al., *Biochemistry Int.*, 25:767–773 (1991). The oligonucleotide sequence utilized, CGTTCCTCCTGU, was complementary to the splicing site at 983–994 of the Herpes Simplex Virus 1 ("HSV-1"). As a control, an equivalently modified sequence (AGCAAAAGCAGG) complementary to the RNA produced by influenza virus was utilized. The oligonucleotides were applied to HSV-1 infected cells in either the complexed or the free state. When a complex was utilized, the complex was formed with the diblock copolymer of formula (XIX) (polyoxyethylene-poly(L-alanine-L-lysine), wherein i was equal to 44 and j was equal to 8). Oligonucleotide complexes were formed as described in Example 6.

African marmoset kidney cells ("Vero" cells) were infected with HSV-1 virus (strain L2, obtained from the Museum of Virus Strains, D. I. Ivanovskii, *Inst. of Virol.*, Russian Federation), as described by Vinogradov et al., *BBRC*, 203:959 (1994). The infected cells were washed with PBS. After washing, fresh RPMI-L 640 media containing 10% of fetal calf serum and free or complex oligonucleotide was added to the cell. The cells were then incubated at 37° C. under 5% $CO_2$ for 24 hours. The HSV-1 infectivity of the of the cell media was then determined using the patch production method described by *Virology, A Practical Approach*, Mahy, Ed., IRL Press, Washington, D.C., 1985.

The results, utilizing varying concentrations of oligonucleotide, were as follows:

| Oligo Conc. | HSV-1 Infectious Titre (CPE$_{50}$/ml) (n = 7) | | |
|---|---|---|---|
| Treatment | 0.2 µM | 1.0 µM | 5.0 µM |
| Control (un-treated infected cells) | 1.0 (±0.5) × 10$^6$ | 1.0 (±0.5) × 10$^6$ | 1.0 (±0.5) × 10$^6$ |
| Anti-HSV complex | 1.4 (±0.2) × 10$^2$ | 0.5 (±0.3) × 10$^2$ | 0 |
| Anti-influenza complex | 1.0 (±0.6) × 10$^6$ | 0.7 (±0.1) × 10$^6$ | 0.8 (±0.2) × 10$^6$ |
| Free Anti-HSV | 0.9 (±0.4) × 10$^5$ | 2.3 (±0.7) × 10$^3$ | 1.6 (±0.4) × 10$^2$ |
| Free Anti-Influenza | 1.1 (±0.4) × 10$^6$ | 0.9 (±0.2) × 10$^6$ | 0.6 (±0.3) × 10$^6$ |

EXAMPLE 10

Antisense Oligonucleotide Designed to Inhibit Herpes Virus

Unless otherwise noted, this example utilized the same procedures as were utilized in Example 9. The cells utilized were BHK cells, a Chinese hamster kidney cell line. When the complexed form of the oligonucleotides was used, the complex was formed with the diblock copolymer of formula (XVII) (polyoxyethylene-poly-L-lysine, wherein i was 44 and j was 30), using the procedure described in Example 6. The concentration of the stock solution of complex was 0.09 OD$_{260}$/µl. The ratio of polycation block imino and amino groups to oligonucleotide phosphates was 10. The oligonucleotides, in complexed or free form, were applied to the cells at a concentration of 3.0 µM. The results were as follows:

| Treatment of cells | HSV-1 infectious titre (CPE$_{50}$/ml) n = 7 |
|---|---|
| Control (untreated infected cells) | 10 (±3) × 10$^3$ |
| Anti-HSV complex | 8 (±6) |
| Anti-influenza complex | 13 (±4) × 10$^3$ |
| Free Anti-HSV | 50 (±14) × 10$^2$ |
| Free Anti-influenza | 9 (±2) × 10$^3$ |

EXAMPLE 11

In Vivo Inhibition of HSV

Polynucleotide complexes between the block copolymer of formula (XVII) (polyoxyethylene-poly-L-lysine, wherein i was 44 and j was 30) and the Anti-HSV and Anti-Influenza oligonucleotides were formed using the methods outlined in Example 9. The concentration of the stock solutions of complexes was 0.9 OD$_{260}$/µl. The ratio of polycation block imino and amino groups to oligonucleotide phosphates was 10.

Inbred white mice (body weight: 6 to 7 g) were infected with HSV-1 (strain C1 from Belorussian Res. Inst. of Epidemiol. & MicrobioL, Minsk) by intraperitoneal injection of 30 µl of a virus suspension (titre: 10$^{-7}$ LD$_{50}$/ml).

Either Anti-HSV complex, Anti-influenza complex, free Anti-HSV or free Anti-Influenza were injected (10 µl) into the tail vein of a given mouse at each of 2, 12, 24, 48 or 72 hours post-infection. The results were as follows:

| Treatment of mice | Survived animals/ Amount of Animals in a group | | | % Survival |
|---|---|---|---|---|
| | Exp. 1 | Exp. 2 | Exp. 3 | |
| Control (infected mice) | 1/9 | 1/10 | 2/10 | 13.7 |
| Anti-HSV complex | 8/9 | 6/10 | 7/10 | 73.0 |
| Anti-influenza complex | 2/10 | 0/10 | 1/10 | 10.0 |
| Free Anti-HSV | 1/10 | 1/10 | 0/10 | 7.0 |
| Free Anti-influenza | 0/9 | 1/10 | 0/10 | 7.0 |

EXAMPLE 12

Plasma Life of Polynucleotide Complex

A$^{32}$P-labelled 17-mer (GGCTCCATTTCTTGCTC) complementary to the transcription initiation site of the HIV-1 tat gene was utilized in this example. The oligonucleotide was modified at its 5'-end with cholesterol as described by Boutorin el al., *Bioconjugate Chemistry*, 2: 350–356 (1990). A polynucleotide conjugate of the oligonucleotide was formed with the block copolymer of formula (XX) polyoxyethylene-poly(propyleneimine/butyleneimine), wherein i was 44 and j was to 10). The concentration of the stock solution (dissolved in PBS) of complex was 0.18 OD$_{260}$/µl. The ratio of polycation block imino and amino groups to oligonucleotide was 50.

Male C57/B1/6 mice (weight: 20–24 g; obtained from the Russian Research Center of Molecular Diagnostics and Therapy, Moscow) received 50 µl intravenous injections of Anti-HIV conjugate or free Anti-HIV, at 0.18 OD$_{260}$/µl dissolved in PBS. At defined times after the injections, blood sample were taken from the tail vein and the animals were sacrificed. The amount of radioactive material in blood or tissue sample was determined by liquid scintillation counting (after appropriate solubilizations). The results were as follows:

| Time after injection (min) | Plasma levels (% of injected dose) | | Liver levels (% of injected dose) Prep. A | Liver levels (% of injected dose) Prep. B |
|---|---|---|---|---|
| | Anti-HIV Conjugate | Free Anti-HIV | | |
| 0 | 100 | 100 | 0 | 0 |
| 5 | 95 | 58 | 3 | 7 |
| 10 | 91 | 40 | 5 | 19 |
| 15 | 84 | 33 | 7 | 26 |
| 20 | 79 | 27 | 9 | 30 |
| 30 | 75 | 20 | 10 | 35 |

EXAMPLE 13

Cationic Block Copolymer Synthesis 1,4-dibromobutane (5.4 g, 25 mmoles, from Aldirich Co., Milwaukee, Wis.) was added to a solution of N-(3-aminiopropyl)-1,3-propanediamine (6.55 g, 50 mmoles, from Aldrich Co.) dissolved in 100 ml of 1,4-dioxane. This reaction mixture was stirred at 20° C. for 16 h. The product of this reaction spontaneously precipitates from solution as the hydrobromide salt. This precipitated first intermediate was collected and twice dried by rota-evaporation from a solution of 10% triethylamine in methanol. This evaporation procedure was effective to remove substantial amounts of the bromide salt. The first intermediate was dissolved in 50 ml of 1,4-dioxane and reacted with 2.7 g (12.5 mmoles) of 1,4-dibromobutane. Again, the reaction proceeded for 16 h at 20° C., and the resulting second intermediate was recovered and dried as above.

The second intermediate was neutralized with acetic acid to a pH of 7–8 and purified by gel filtration on Sephadex G-25, using an aqueous eluent. Three major polyimine fractions were obtained, having apparent molecular weights of 1060, 700 and 500, respectively.

Poly(oxyetheleneglycol) (1.5 g, M.W. 1500, from Fluka) was dissolved in 8 ml of 1,4-dioxane and reacted with 0.17 g (1 mmole) of N,N'-carbonylimidazole (Aldrich Co.) at 20° C. for 3 h. The reaction mixture was divided into two parts. Each part was mixed with 4 ml of a 10% (w/v) solution of either the 1060 or 700 MW polyimine fraction, which solution further contained 0.01 N NaOH. The mixture was stirred for 16 h at 20° C. From this mixture, block copolymers of formula (XX) and various MW ranges were isolated by gel filtration.

EXAMPLE 14

Cationic Block Copolymer Synthesis 0.5 g of a succinimidyl carbonate of methoxy-PEG (MW 5000, Shearwater Polymers, Inc., USA) was dissolved in 1,4-dioxane. This dioxane solution was added to an aqueous solution containing 0.2 g of the 1060 MW polyimine polymer described above, which aqueous solution further included
0.01 N NaOH. This reaction mixture was stirred at 20° C. for 16 h. A polymer of formula (XXII) was isolated from the reaction by gel filtration.

EXAMPLE 15

Cationic Block Copolymer Synthesis 1.5 g of poly(oxyetheleneglylol) (MW 8000, Fluka) were dissolved in 8 ml of 1,4-dioxane. 0.34 g (2 mmole) of N,N'-carbonylimidazole (Aldrich Co.) were added to the solution and reacted for 3 h at 20° C. 8 ml of an aqueous solution containing 0.01 N NaOH and 15% (w/v) of the 500 MW polyimine polymer described above in Example 13 was then added to the first reaction mixture. The resulting mixture was reacted for 16 h at 20° C. with stirring. A polymer of formula (XXIII) was isolated from the second reaction mixture by gel filtration.

EXAMPLE 16

Conjugate Synthesis with Oligonucleotide

A 12-mer oligonucleotide, 5'-CGTTCCTCCTGU ("Oligo A") complimentary to the splicing site (positions 983–994 on the viral genome) of the early mRNA of type 1 Herpes Simplex Virus ("HSV-1"), was synthesized using a 380B-02 DNA-synthesizer (Applied Biosystems, CA). The synthesizer used phosporamidite chemistry and an 8 min. synthesis cycle. Cycle conditions and preparation of the crude product were done as recommended by Applied Biosystems. The crude Oligo A obtained from the synthesis was precipitated from a 1 M LiCl solution (0.5 ml) with acetone (2 ml). The precipitate was dissolved in triethylammonium acetate buffer and purified by reverse-phase high performance liquid chromatography on a Silasorb C18 column (9×250 mm, Gilson, France) developed with an acetonitrile gradient in a 20 mM TEAA buffer (p H 8.5).

The 3'-terminal of the purified Oligo A was oxidized with periodate to create an aldehyde and conjugated by reductive alkylation with a hexamethylene-diamine linker, creating an amine derivative. See Che-Chung et al., *Biochem. Intemat.*, 25:767 (1991); Vinogradov el al., BBRC, 203:959 (1994). "Pluronic A", a block copolymer of formula (XIV)(x=25, y+38, z=25) was similarly oxidized to create terminal aldehydes. The amine derivative (1 mg) was dissolved in 100 μl of 0.1 M borate buffer (pH 9.0) and mixed with 2 mg of the Pluronic A derivative. 1.5 mg of sodium cyanoborohydride was added to the mixture to reduce the Schiff's bases formed between the amine and aldehyde groups. This reaction was allowed to proceed for 12 hours at 4° C. The polymeric product of this reaction was isolated by gel filtration chromatography on Sephadex LH-20, utilizing 90% aqueous isopropanol as the eluent. The conjugate so obtained is referred to hereinafter as "Oligo A Conjugate."

EXAMPLE 17

The Effect of Oligo A Conjugate on Virus Production

Oligo A and Oligo A Conjugate were separately dissolved in RPMI 1640 medium (ICN Biomedicals Inc., Costa Mesa, Calif.) to a final concentration of 0.2 mM (based on oligonucleotide absorbance). These stock solutions were then filtered through 0.22 μm filters to remove any possible bacterial or fungal contamination.

Monolayers of Vero cells were incubated for 1 hour at 37° C. in serum-free RPMI 1640 together with various concentrations of Oligo A or Oligo A Conjugate. The monolayers, while still exposed to oligonucleotides, were then infected with 1 plaque forming unit per cultured cell of HSV-1, strain L2 (from the Museum of Virus Strains of the D. I. Ivanovskii Institute of Virology, Russian Academy of Sciences, Russian Federation). This infection method has been described by Vinogradov et al., *BBRC*, 203:959 (1994). After 8 hours of exposure to virus and oligonucleotides, the medium on the cells was replaced with fresh medium containing 10% FCS. Medium from the cells was collected at 22 and 39 hours after the ineffective incubation, and the virus titer in the collected medium was determined as described in *Virology, A Practical Approach*, Mahy, Ed., IRL Press, Oxford Univ. Press, Washington, D.C., 1985. The results were as follows:

| Sample | Oligonucleotide | Infectious Titer of HSV-1 (PFU/ml) | |
|---|---|---|---|
| concentration (mM) | concentration (μM) | 22 hours past infection | 39 hours past infection |
| Control (cells without oligo-nucleotides) | 0 | $5 \times 10^6$ | $1 \times 10^7$ |
| Oligo A | 10 | $3 \times 10^6$ | $5 \times 10^6$ |
|  | 5 | $5 \times 10^6$ | $1 \times 10^7$ |
|  | 2 | $5 \times 10^6$ | $1 \times 10^7$ |
|  | 1 | $5 \times 10^6$ | $1 \times 10^7$ |
| Oligo A Conjugate | 10 | 0 | 0 |
|  | 5 | 0 | $5 \times 10^2$ |
|  | 2 | $1 \times 10^3$ | $7 \times 10^3$ |
|  | 1 | $5 \times 10^4$ | $3 \times 10^6$ |

EXAMPLE 18

Synthesis of a Phosphonate Monomer 40 mmoles of butanediol-1,3 (Merck) dissolved in 50 ml of anhydrous pyridine (Aldrich) were reacted with 20 mmoles 4,4'-dimethoxytritylchloride (Sigma) for 1.5 hours at 20° C. The reaction was monitored using thin layer chromatography on the silicagel plates (Merck) developed with a chloroform:methanol (95:5). The Rf of the product was 0.6. The reaction mixture was added to 200 ml of an 8% aqueous solution of the sodium bicarbonate and the product extracted with chloroform. The chloroform extract was evaporated in vacuum and the resulting oily first intermediate was used in the next stage of the synthesis.

12 mmoles of first intermediate were dissolved in 30 ml of ahydrous 1,4-dioxane, containing 3.14 ml (18 mmoles) of diisopropylethylamine (Aldrich). 18 mmoles of salicylchlorophosphite (Sigma) dissolved in 10 ml of ahydrous 1,4-dioxane were added to the diisopropyethylamine solution in small portions under an inert, argon atmosphere. The reaction mixture was incubated during 1 hour at 20° C. The reaction was monitored by the thin layer chromatography as described above. The Rf of the product was 0.05. 10 mls of water were added to the reaction mixture. After 30 min., the solvent was evaporated. The product was dissolved in 100 ml of chloroform and the solution obtained was washed stepwise with (1) 100 ml of 8% aqueous solution of the sodium bicarbonate, (2) 100 ml of 0.2 M triethyammoniumacelate solution (pH 7.2), and (3) 100 ml of water. The organic solvent was evaporated and the oily remainder, containing the phosphonate monomer was purified by chromatography on silicagel column, using stepwise gradient of (1) chloroform, (2) 3% methanol in chloroform and (3) 6% methanol in chloroform. The yield of the monomer was 4.1 g (=7.3 mmol, 63%). The product, having structure

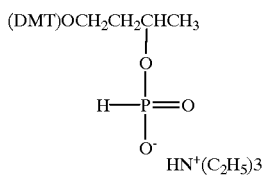

wherein DMT represents a dimethoxytrityl group, can be termed "Phosphonate Monomer A."

EXAMPLE 19

Synthesis of Polycation BDP

A 0.05 M solution of the phosphonate Monomer A in anhydrous pyridine:acetonitrile mixture (1:1) was placed in the position 6 of the DNA-synthesator (model 380-B02, Applied Biosystems, CA). A 2% solution of adamantoilchloride (Sigma) in the mixture acetonitrile:pyridine (95:5) was used as a condensing agent. The synthesis was conducted using the program modified for an H-phosphonate cycle (Sinha and Striepeke In: *Oligonucleotides and Analogues: A Practical Approach,* Eckstein Ed. IRL Press, Oxford, N.Y.-Tokyo, p.185, 1991) and the DMT-group was preserved after the synthesis was complete. Adenosine (4 μmoles) immobilized on a standard CPG-500 solid support was used as a first unit during the polymer synthesis (Vinogradov et al. *BBRC,* 203, 959 (1994). The synthesizer was programmed to add Phosphonate Monomer A repeating units to the adenosine monomer. Following all synthesis steps, the H-phosphonate groups on the immobilized substrate were oxidized with the solution of 104 mg of hexamethylenediamine (Sigma) in 0.6 ml of a mixture of anhydrous pyridine:$CCl_4$ (5:1) applied for 15 min. at 20° C., then the carrier was washed with the pyridine:acetonitrile mixture (1:1).

Deblocking and cap removal was achieved by ammonolysis (*Oligonucleotides and Analogues. A Practical Approach,* Eckstein Ed. IRL Press, Oxford, N.Y.-Tokyo, 1991). The product was purified by HPLC using Silasorb C, column (9×250 mm. Gilson, France) in the acetonitrile gradient (0–80%). The peak, containing dimethoxytritylated-product was collected, the solvent was evaporated and the remainder was treated with 80% acetic acid (20 min). The acetic acid was evaporated and the polycation was purified again by HPLC. The yield of the 15-mer (counted in terms of Phosphonate Monomer A) is 50% (2.2 μmoles). This created a polymer according to formula A. The polymer will be termed hereinafter "BDP."

EXAMPLE 20

Solid Phase Synthesis of the Diblock Copolymer Polyoxyethylene-BDP

Dimethoxytrityl-polyethyleneoxide-H-phosphonate was synthesized as described in Example 18 using polyethyleneglycol (1500 M.W. from Fluka) instead of butanediol-1, 3. The BDP polycation was synthesized as described in Example 19, except that, at the last stage of the chain growth, dimethoxytrityl-polyethyleneoxide-H-phosphonate was introduced as the last building block. The H-phosphonate groups of the block copolymer were oxidized as described in Example 19 using tetramethylenediamine (Sigma) instead of hexamethylenadiamine, resulting in the formation of phosphonamide bonds between the diamines and the backbone phosphates.

EXAMPLE 21

Solid Phase Synthesis of the Oligonucleotide-BDP Diblock Copolymer

A diblock copolymer comprising 12-mer oligonucleotide, 5'-GGTTCCTCCTGU (Oligo A, complementary to the splicing site of the early mRNA of type 1 Herpes Simplex Virus (HSV-1), Vinogradov et al. *BBRC,* 203, 959 (1994)) and the BDP polymer was synthesized in DNA synthesator. First the BDP polymer was synthesized as described in Example 19, except that it was not removed from the support. Then the oligonucleotide chain was synthesized step-wise onto BDP polycationic polymer linked to the solid state support using the standard phosphoroamidite chemistry as described by Vinogradov et al. *BBRC,* 203, 959 (1994). The H-phosphonate groups of the diblock copolymer were oxidized as described in Example 19 using tetamethylenediamine (Sigma) instead of hexamethylenediamine.

EXAMPLE 22

Effect of Oligonucleotide-BDP Diblock Copolymer on Viral Growth

The experiment was performed exactly as described in Example 17 except that (1) the oligonucleotide-BDP copolymer of Example 21 was used and (2) a single concentration of oligonucleotide-BDP copolymer (conjugate) was used (4,4M).

| Sample | Virus titre after 39 hours |
|---|---|
| Control (without oligonucleotide) | $500 \times 10^4$ |
| Nonmodified Oligo A | $500 \times 10^4$ |
| Diblock | $5 \times 10^4$ |

EXAMPLE 23

Synthesis of Branched Polyimine Polycation

A. The polyimine polycation ("polyspermine") was obtained by stepwise polycondensation of N-(3- aminopropyl)-1,3-propanediamine and 1,4-dibromobutane as described in Example 13 and used without conjugating to poly(ethylene glycol).

B. The polyimine polycation synthesized in A was modified by dansyl chloride to obtain a fluorescent dansyl-labeled substance, purified by thin layer chromatography and a major component of the mixture (over 75% in most batches) was analyzed by electrospray mass-spectrometry in positive charge mode. The results were compared with mass-spectra obtained for the N-(3-aminopropyl)-1,3-propanediamine modified with dansyl chloride. Dansyl-labeled N-(3-aminopropyl)-1,3-propanediamine gave a four-modal peak at M+1, M+2, M+3 and M+4 (667.6, 668.5, 669.6 and 670.5). In the spectrum of the polycondensation products there were observed two types of polymodal peaks: M and M+54. For M-peaks two distinct groups were observed, with M/2H+ and M/H+, equal to 598.5 and 1195.6 respectively. This molecular mass was very close to a linear polycation with 12 nitrogen atoms (1221). M+54 peaks at 1249.8 and 652.5 correspond to a polycation with $CH_2CH_2CH_2CH_2$ cross-links.

C. 1H-NMR spectra were obtained for the samples of the polyimine polycation synthesized in A and dissolved in DMSO. Three groups of signals were observed at 1.40–1.80 ppm (Ha), 1.80–2.20 ppm (Hb) and 2.35–2.80 ppm (Hc). Ha related to $CH_2CH_2CH_2CH_2$ protons, Hb related to $CH_2CH_2CH_2$ protons, Hc related to —$NHCH_2$ and protons. Integration of resonance signals for these three groups gave a ratio Ha:Hb:Hc equal to 1.00:0.75:1.20. The theoretical ratio for linear polycations with 12 nitrogen atoms is 1.00:1.33:3.67. Increase in Hb:Ha and Hc:Ha ratios suggested presence of branched structures with a mixture of primary, secondary and tertiary amines.

D. The concentration of primary amino groups in the polyimine polycation synthesized in A was determined by fluorescamine method as described by Weigele et al., *J. Amer.Chem.Soc.,* 1972, 94:5927. The total amount of primary, secondary, and tertiary amino groups in the polycondensation product was determined using potentiometric titration. The ratio of the total amount of primary, secondary, and tertiary aminogroups to the amount primary aminogroups equals 2.7. Given the molecular masses of the condensation product determined using mass-spectrometry the result of this experiment suggests considerable branching, i.e. the presence of tertiary amines.

EXAMPLE 24

Synthesis of Linear Polyimine Polycation

Linear polycations of polyimine type are synthesized by condensation of a diaminoalkyl and bis-aldehyde in the presence of sodium cyanoborohydride using a modified reductive amination procedure described by Aziz et al., *J. Pharmac. Exper. Therapeutics,* 1995, 274:181. 0.33 g of malonaldehyde bis(dimethyl acetal) was added in 10 ml of 0.5 N HCl and stirred for 1 h at 20° C. to obtain free bis-aldehyde. 1.27 g of N,N'-bis[3-aminopropyl]-1,4-butanediamine was added to this solution and pH was adjusted to 5.0. The mixture was allowed to stay for 1 h at 37° C., then 1.27 g of N,N'-bis[3-aminopropyl]-1,4-butanediamine was added to it and pH was adjusted to 7.0 using sodium carbonate solution. The reaction mixture was treated with 0.26 g of sodium cyanoborohydride and left for additional 1 h at 37° C. The final slightly yellow solution was desalted by gel permeation chromatography on the Sephadex G-25 column in 10% methanol and first high-molecular weight fractions revealing primary aminogroups in ninhydrine test were freeze-dried. This yields 0.43 g of the following polyimine polycation:

EXAMPLE 25

Synthesis of Cationic Block Copolymer 1.5 g of poly(ethylene glycol), methyl ester, mw. 5000 Mw. (Sigma) was activated by 0.25 g of 1,1'-carbonyldiimidazole in 10 ml of anhydrous acetonitrile for 3 hrs at room temperature. The solvent was evaporated in vacuo, the residue redissolved in water and dialyzed through Membra-Cel MD-25-03.5 membrane with cutoff 3500 Da against water. Desalted solution was concentrated in vacuo and used in a reaction with 2-fold excess of poly-L-lysine, Mw. 4000, in methanol-water solution for 16–24 hrs at room temperature. The conjugate obtained was purified by gel-permeation column chromatography on Sephadex-50 (fine) (Pharmacia) in water and then by reverse phase chromatography on semi-preparative column (Vydac C18 5 u , 10 mm×25 cm) in acetonitrile concentration gradient. The yield was 70%. Content of aminogroups was measured by fluorescamine method and total nitrogen content was determined by elemental analysis to assess the purity of the conjugates. Usually it was about 75–90% based on graviometry.

EXAMPLE 26

Synthesis of Cationic Block Copolymer

Following the procedure of Example 25 but substituting the 2-fold excess of poly-L-lysine by the same excess of polyethyleneimine, $(NHCH_2CH_2)_x[N(CH_2CH_2)CH_2CH_2]_y$, Mw. 2000 (Aldrich Co.) there is obtained 0.4 g of the cationic diblock copolymer:

EXAMPLE 27

Synthesis of Grafted Popolymer

A. 24 g (3 mmol) of poly(ethylene glycol), mw 8000 (Aldrich Co.) were dried by co-evaporation with anhydrous pyridine in vacuo and dissolved in 50 ml of anhydrous acetonitrile. Then 0.5 g (1.5 mmol) of 4,4'-dimethoxytrityl chloride in 30 ml of anhydrous pyridine was added to this solution dropwise under continuous stirring during 30 min. The mixture was allowed to stand for additional 2 h at room temperature, then the solvents were evaporated in vacuo. The residue was dissolved in 50 ml of dichloromethane, extracted with 5% sodium bicarbonate (2×30 ml), and applied on the Silicagel column (3×45 cm, 40–60 μm). Stepwise elution with dichloromethane-methanol solutions separated a slightly yellow mono-4,4'-dimethoxytrityl-derivative of poly(ethylene glycol) with an yield about 75–85%. The side product of the reaction (10–15% yield) was the bis-4,4'-dimethoxytrityl-derivative of poly(ethylene glycol).

B. 1.5 g of mono-4,4'-dimethoxytrityl-derivative of poly (ethylene glycol) obtained in A was activated by 0.25 g of 1,1'-carbonyldiimidazole in 10 ml of anhydrous acetonitrile for 3 hrs at room temperature. The solvent was evaporated in vacuo, the residue redissolved in water and dialyzed through Membra-Cel MD-25-03.5 membrane with cutoff 3500 Da against water. Desalted solution was concentrated in vacuo and then reacted with poly-L-lysine, Mw. 19000 in methanol-water solution for 24 h at room temperature at a molar ratio of poly(ethylene glycol) to free aminogroups of poly-L-lysine 0.7:1.0. The conjugate obtained was purified by gel-permeation column chromatography on Sephadex-50 (fine) (Pharmacia) in water and then by reverse phase chromatography on semi-preparative column (Vydac C18 5 u , 10mm×25 cm) in acetonitrile concentration gradient. This yields a grafted polylysine copolymer at 35% yield in which 50% of free aminogroups are substituted with poly(ethylene glycol) as determined by fluorescamine method.

EXAMPLE 28

Synthesis of Grafted Copolymer

A. 24 g (3 mmol) of poly(ethylene glycol), mw 8000 (Aldrich Co.) were dried by co-evaporation with anhydrous pyridine in vacuo and dissolved in 50 ml of anhydrous acetonitrile. Then 0.5 g (1.5 mmol) of 4,4'-dimethoxytrityl chloride in 30 ml of anhydrous pyridine was added to this solution dropwise under continuous stirring during 30 min. The mixture was allowed to stand for additional 2 h at room temperature, then the solvents were evaporated in vacuo. The residue was dissolved in 50 ml of dichloromethane, extracted with 5% sodium bicarbonate (2×30 ml), and applied on the Silicagel column (3×45 cm, 40–60 μm). Stepwise elution with dichloromethane-methanol solutions separated a slightly yellow mono-4,4'-dimethoxytrityl-derivative of poly(ethylene glycol) with an yield about 75–85%. The side product of the reaction (10–15% yield) was the bis-4,4'-dimethoxytrityl-derivative of poly(ethylene glycol).

B. 1.5 g of mono-4,4'-dimethoxytrityl-derivative of poly (ethylene glycol) obtained in A was activated by 0.25 g of 1,1 '-carbonyldiimidazole in 10 ml of anhydrous acetonitrile for 3 hrs at room temperature. The solvent was evaporated in vacuo, the residue redissolved in water and dialyzed through Membra-Cel MD-25-03.5 membrane with cutoff 3500 Da against water. Desalted solution was concentrated in vacuo and then reacted with polyethylenemine, Mw. 25,000 in methanol-water solution for 24 h at room temperature at a molar ratio of poly(ethylene glycol) to free aminogroups of polyethyleneimine 0.7:1.0. The conjugate obtained was purified by gel-permeation column chromatography on Sephadex-50 (fine) (Pharmacia) in water and then by reverse phase chromatography on semi-preparative column (Vydac C18 5 μm, 10 mm×25 cm) in acetonitrile concentration gradient. This yields a grafted polyethyleneimine block copolymer at 85% in which 45% of free aminogroups are substituted with poly(ethylene glycol) as determined by fluorescamine method as described by Weigele et al. (*J. Amer. Chem. Soc.,* 1972, 94:5927).

EXAMPLE 29

Synthesis of Grafted Copolymer

Following the procedure of Example 28 but using a molar ratio of activated poly(ethylene glycol) to free aminogroups of polyethyleneimine 0.3:1.0, there is obtained in 80% yield a grafted polyethyleneimine copolymer in which 24% of free aminogroups are substituted with poly(ethylene glycol).

EXAMPLE 30

Synthesis of Cationic Block Copolymer

Following the procedure of Example 26 but substituting 6.0 g of polyethyleneglycol, mw 20,000 for the excess of polyethylene glycol, mw 5,000 there is obtained 6.0 g of the cationic block copolymer:

EXAMPLE 31

Synthesis of Cationic Block Copolymer

A. Following the procedure of Example 26 but substituting 1.5 g of polyethyleneglycol, Mw. 5,000 by 2.4 g of polyethyleneglycol, Mw. 5,000 (Aldrich Co.) there is obtained 1.2 g of the cationic block copolymer containing polyethyleneinmine and polyethyleneglycol chain segments.

B. The molecular mass of this block-copolymer was determined by static light scattering method using DAWN multi-angle laser photometer (Wyatt Technology, Santa Barbara, Calif.) which operated at 15 angles and equipped with He-Ne laser (632.8 nm). The samples of the block copolymer were dialyzed through membrane with cutoff 3,500 Da against 4.5× $10^{-3}$ g/ml NaCl and then filtered directly into flow cell used for light scattering experiments. Weigh-average molecular mass was calculated on the base of four measurements. Cell constant was determined by calibration with different concentrations of NaCl. Specific refractive index increment (dn/dc) was measured using Wyatt/Optilab 903 interferometric refractometer at 632.8 nm. The molecular mass of the sample obtained was 16,000, suggesting that this polymer contained approximately one polyethyleneinmine segment and two polyethyleneglycol segments.

C. The number of the primary aminogroups in the synthesized sample of the copolymer was determined using a modified procedure described by Weigele et al. (*J.Amer.Chem.Soc.,* 1972, 94:5927). To 1.5 ml of a sample in 20 mM sodium borate, pH 9.5 (aminogroups concentration up to 100 uM) 0.25 ml of fluorescamine solution (0.024%, Sigma) in acetone was added and vortexed for 5 min. The measurements have been made on spectrofluorometer Shimadzu at excitation wavelength 384 nm and at 430 to 510 nm emission wavelength range. Extinction coefficient at emission 475 nm was determined as equal to $1.58 \times 10^6$ $M^{-1}$. The specific amount of primary aminogroups was 0.69 mmol/g.

EXAMPLE 32

Synthesis of Grafted Copolymer

Following the procedure of Example 28 but substituting 24 g of poly(ethylene glycol) by the same amount of Pluronic L61 (BASF Co.) and using a molar ratio of activated Pluronic L61 to free aminogroups of polyethyleneimine 0.3:1.0, there is obtained in 22% yield a grafted polyethyleneimine copolymer in which 8% of free aminogroups are substituted with Pluronic L61.

EXAMPLE 33

Synthesis of Grafted Copolymer

Following the procedure of Example 28 but substituting 24 g of poly(ethylene glycol), by the same amount of Pluronic P85 and using a molar ratio of activated Pluronic P85 to free aminogroups of polyethyleneimine 0.3:1.0 there is obtained in 70% yield a grafted polyethyleneimine copolymer in which 11% of free aminogroups of polyethyleneimine are substituted with Pluronic P85.

EXAMPLE 34

Synthesis of Grafted Copolymer

Following the procedure of Example 28 but substituting 24 g of poly(ethylene glycol), by the same amount of Pluronic L123 (BASF Co.) and using a molar ratio of activated Pluronic L123 to free aminogroups of polyethyleneimine 0.3:1.0 there is obtained in 30% yield a grafted polylysine copolymer in which 9% of free aminogroups are substituted with Pluronic L123.

EXAMPLE 35

Synthesis of Grafted Copolymer

Following the procedure of Example 28 but substituting 24 g of poly(ethylene glycol), by the same amount of Pluronic F38 (BASF Co.) and using a molar ratio of activated Pluronic F38 to free aminogroups of polyethyleneimine 0.3:1.0 there is obtained in 40% yield a grafted polylysine copolymer in which 9% of free aminogroups are substituted with Pluronic F38.

EXAMPLE 36

Synthesis of Multi-Grafted Copolymer

Following the procedure of Example 28 but substituting polyethyleneimine by polyethyleneimine modified with Pluronic L123 (BASF Co.) obtained in Example 35 and using a molar ratio of activated poly(ethylene glycol) to free aminogroups of modified polyethyleneimine 0.4:1.0 there is obtained in 20% yield a grafted polyethyleneimine copolymer in which 9% of free aminogroups are substituted with Pluronic L123 and 30% of groups are substituted with poly(ethylene glycol).

EXAMPLE 37

Complex with Oligonucleotide

A. Model phosphorothioate oligodeoxyribonucleotide PS-dT20 was synthesized using ABI 291 DNA Synthesizer (Applied Biosystems, San Diego, Calif.) following the standard protocols. After ammonia deprotection the oligonucleotide was twice precipitated by ethanol and then used without purification.

B. The complex formed between the PS-dT20 and polyethyleneimine-poly(ethylene glycol) block copolymer obtained in Example 28 was obtained by mixing the aqueous solutions of these polymers in 10 mM phosphate buffer, pH 7.4 so that the ratio of the primary amino groups of the block copolymer to the phosphate charges of the PS-dT20 was 1.0. All solutions were prepared using double distilled water and were filtered repeatedly through the Millipore membrane with pore size 0.22 $\mu$M.

C. The electrophoretic mobility (EPM) and the size of the particles of the complex synthesized in B were determine. The EPM measurements were performed at 25° C. with an electrical field strength of 15–18 V/cm using "ZetaPlus" Zeta Potential Analyzer (Brookhaven Instrument Co.) with 15 mV solid state laser operated at a laser wavelength of 635 nm. The zeta-potential of the particles was calculated from the EPM values using the Smoluchowski equation. Effective hydrodynamic diameter was measured by photon correlation spectroscopy using the same instrument equipped with the Multi Angle Option. The sizing measurements were performed at 25° C. at an angle of 90°. The zeta potential of this sample was close to zero, suggesting that particles were electroneutral. The average diameter of the particles was 35 nm.

EXAMPLE 38

Stability Against Nuclease Digestion

100 $\mu$g of the complex formed between the PS-dT20 and polyethyleneimine-poly(ethylene glycol) block copolymer obtained in Example 39 was treated by 1 mg of snake venom phosphodiesterase (Phosphodiesterase I from *Crotalus adamanteus*, 0.024 units/mg, Sigma) for 2 and 18 hrs at 37° C. Reaction mixtures were analyzed by gel permeation HPLC for digested PS-dT20. The digestion of the PS-dT20 in this complex was less than 5%. In contrast, free PS-dT20 treated with the same concentration of enzyme for the same time interval was digested completely.

EXAMPLE 39

Accumulation of Oligonucleotide in Caco-2 Monolayers

A. A 5'-aminohexyl PS-dT20 oligonuclectide was synthesized using ABI 291 DNA Synthesizer (Applied Biosystems, San Diego, Calif.) following the standard protocols. After ammonia deprotection the oligonucleotide was twice precipitated by ethanol and then used without purification. 5'-Aminohexyl PS-dT20 was labeled by reaction with fluorescein isothiocyanate (Sigma) following the manufacturer protocol. Fluorescein-labeled PS-ODN was separated from unreacted fluorophore using a Pharmacia PD-10 size exclusion.

B. The complex formed between the fluorescein-labeled PS-dT20 and polyethyleneimine-poly(etbylene glycol) block copolymer was synthesized as described in Example 37 but using fluorescein-labeled PS-dT20 instead of PS-dT20.

C. Caco-2 cells, originating from a human colorectal carcinoma (Fogh et al. J. Natl. Cancer Inst., 59:221–226, 1977) were kindly provided by Borchardt R. T. (The University of Kansas, Lawrence, Kans.). The cells were maintained in Dulbecco's Modified Eagle's Medium (DMEM), containing 10% heat-inactivated fetal bovine serum (FBS), 1% non-essential amino acids, benzylpenicilin (100 U/ml) and streptomycin (10 ug/ml), in an atmosphere of 90% air and 10% $CO_2$ as described by Artursson (J. Pharm. Sci., 79:476–482, 1990). All tissue culture media were obtained from Gibco Life Technologies, Inc. (Grand Island, N.Y.). The cells were grown on collagen coated polycarbonate filter chamber inserts (Transwell, Costar Brand Tissue Culture Products, Contd.; pore size 0.4 um; diameter 24.5 mm). 250,000 cells were added to each insert and cells of passage number 32–45 were used. The cells were fed every second day and were allowed to grow and differentiate for up to 14 days before the monolayers were used in the following absorbtion experiments.

D. Caco-2 cell monolayers were preincubated for 30 min. at 37° C. with assay buffer, containing sodium chloride (122 mM), sodium bicarbonate (25 mM), glucose (10 mM), HEPES (10 mM), potassium chloride (3 mM), magnesium sulfate (1.2 mM), calcium chloride (1.4 mM) and potassium phosphate dibasic (0.4 mM). After this, the assay buffer was removed and the cells were exposed to 50 μM fluorescein-labeled PS-ODN or its complex in the assay buffer for 90 min at 37° C. After that the dye solutions were removed and cell monolayers were washed three times with ice-cold PBS. Cells were then solubilized in 1.0% Triton X-100 and aliquots (25 μl) were removed for determination of cellular fluorescence using a Shimadzu RF5000 spectrofluorometer at $\lambda$ex=488 nm, $\lambda$em=520 nm. Samples were also taken for protein determination using the Pierce BCA method. The amounts of fluorescein-labeled PS-dT20 absorbed by the cells was as follows:

| Sample | Cellular accumulation of oligonucleotide, nmol/mg protein |
|---|---|
| Free fluorescein-labeled PS-dT20 | 0.14 ± 0.03 |
| The complex | 0.5 ± 0.01 |

This demonstrates that incorporation of polynucleotide in the complex with the block copolymer increases cellular accumulation of polynucleotide by more than 3-times.

EXAMPLE 40

Transport of Oligonucleotide Across Caco-2 Monolayers

A. The filter-grown Caco-2 monolayers were used for oligonucleotide permeability studies after complete maturation, i.e., as from day 14 after plating. Filters were gently detached from the wells and placed in Side-Bi-Side diffusion cells from Crown Bio Scientific, Inc. (Somerville, N.J.) maintained at 37° C.±0.1° C. This system is used as an in viro model of human intestinal epithelium to evaluate oral bioavailability of drugs (Pauletti et al. Pharm. Res. 14:11–17, 1977). Cell monolayers were preincubated for 30 minutes at 37° C. with the assay buffer, containing 10% heat-inactivated fetal bovine serum (FBS), 1% non-essential amino acids, benzylpenicilin (100 U/ml) and streptomycin (10 ug/ml), added to both donor and receptor chambers (3 ml). After preincubation, the assay buffer in the receptor container was replaced by the fresh one, while the assay buffer in the donor container was replaced by 50 μM fluorescein-labeled PS-ODN or its complex in the assay buffer. To account for the integrity of the monolayers the R123 solutions in the donor container also contained $H^3$-labeled manitol, a paracellular marker (Dawson, J. Membrane Biol., 77) 213–233, 1977) obtained from DuPont Corp. (Boston, Mass.). At 120 min. the solutions in the receptor chamber were removed for determination of fluorescein-labeled PS-ODN using a Shimadzu RF5000 fluorescent spectrophotometer ($\lambda$ex=488 nm, $\lambda$em=520 nm) and $H^3$-manitol determination using a liquid scintillation counter (Hewlett Packard Instruments). Immediately after collecting the solutions in the receptor chamber 3 ml of fresh assay buffer was added to this chamber. The transport of fluorescein-labeled PS-ODN (or manitol) across Caco-2 cell monolayers was expressed as a percentage of the total fluorescein-labeled PS-ODN (or manitol) accumulated in the receptor chamber to the initial amounts of fluorescein-labeled PS-ODN (or manitol) in the donor chamber. A minimum of three different membranes was studied for each drug composition at multiple time points for each membrane. The results were as follows:

| Sample | PS-dT20 transport, % | Manitol transport, % |
|---|---|---|
| Free fluorescein-labeled PS-dT20 | 0.001 ± 0.0005 | 4.0 ± 0.1 |
| The complex | 0.075 ± 0.005 | 4.2 ± 0.02 |

This demonstrates that incorporation of polynucleotide in the complex with the block copolymer increases transport of this polynucleotide across Caco-2 monolayers by more than 7-times while the transport of paracellular is not affected.

What is claimed is:
1. A composition comprising a polynucleotide and a polymer of a plurality of covalently bound polymer segments, wherein the polynucleotide and polymer are not linked covalently; and the polymer segments comprise:
(a) at least one polycation segment which is a cationic homopolymer, copolymer, or block copolymer or a quaternary salt thereof wherein the copolymer comprises at least one aminoalkylene monomer selected from the group consisting of:
(i) a tertiary amino monomer of the formula:

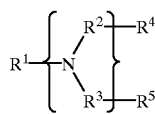

A.

and
(ii) a secondary amino monomer of the formula:

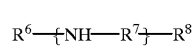

B.

in which:
each of $R^1$, $R^4$, $R^5$, $R^6$, and $R^8$, taken independently of the other, is hydrogen, alkyl of 2 to 8 carbon atoms, another A monomer, or another B monomer;
each of $R^2$, $R^3$, and $R^7$, taken independently of the other, is a straight or branched chain alkanediyl of the formula:

in which z has a value of from 2 to 8; and
(b) at least one straight or branched chained polyether segment of from about 5 to about 400 monomeric units which polyether segment is:
(i) a homopolymer of a first alkyleneoxy monomer —$OC_nH_{2n}$— or
(ii) a copolymer or block copolymer of said first alkyleneoxy monomer and a second different alkyleneoxy monomer —$OC_mH_{2m}$—,
in which
n has a value of 2 or 3 and m has a value of from 2 to 4.

2. The composition according to claim 1 further comprising a targeting molecule.

3. The composition according to claim 1 further comprising a surfactant.

4. The composition according to claim 3, wherein said surfactant is cationic, nonionic, or zwitterionic.

5. A composition comprising a polynucleotide and at least one polyoxyethylene-polyoxypropylene block copolymer, wherein said block copolymer is present in amounts insufficient for gel formation and wherein said polynucleotide and said polymer are not linked covalently.

6. A composition comprising a polynucleotide and a polyoxyethlyene-polyoxypropylene polymer, wherein said polynucleotide and said polymer are not linked covalently, the polymer concentration is below about 15% by weight of the composition, and the composition forms micelles.

7. The composition of claim 6 wherein the polymer concentration is below about 10%.

8. The composition of claim 7 wherein the polymer concentration is below about 5%.

9. The composition of claim 5 wherein the polynucleotide is DNA.

10. The composition of claim 5 wherein the polynucleotide is RNA.

11. The composition of claim 5, wherein at least one of the block copolymers has the formula:

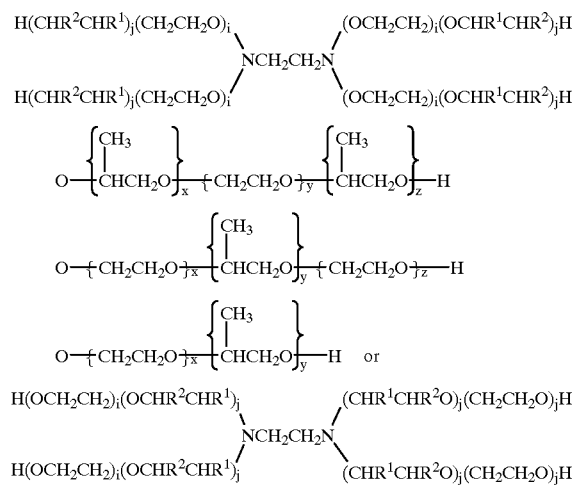

in which x, y, z, i, and j have values from about 2 to about 400, and wherein for each $R^1$ and $R^2$ pair, one of $R^1$ and $R^2$ is hydrogen and the other of $R^1$ and $R^2$ is methyl.

* * * * *